(12) United States Patent
Hosomi

(10) Patent No.: US 8,877,910 B2
(45) Date of Patent: Nov. 4, 2014

(54) PROBE FOR DETECTING POLYMORPHISM IN EXON 12 OF NPM1 GENE AND USE THEREOF

(75) Inventor: Toshiya Hosomi, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 13/458,832

(22) Filed: Apr. 27, 2012

(65) Prior Publication Data

US 2012/0276534 A1 Nov. 1, 2012

(30) Foreign Application Priority Data

Apr. 28, 2011 (JP) .................................. 2011-102327

(51) Int. Cl.
*C07H 21/02* (2006.01)
*C07H 21/04* (2006.01)
*C12Q 1/68* (2006.01)
*C12P 19/34* (2006.01)

(52) U.S. Cl.
CPC ........ *C12Q 1/6886* (2013.01); *C12Q 2600/156* (2013.01)
USPC ....... 536/23.1; 536/24.3; 536/24.33; 435/6.1; 435/91.2

(58) Field of Classification Search
None
See application file for complete search history.

(56) References Cited

U.S. PATENT DOCUMENTS

| 6,492,121 B2 | 12/2002 | Kurane et al. |
| 7,354,707 B2 | 4/2008 | Kurane et al. |

FOREIGN PATENT DOCUMENTS

| EP | 1046717 A2 | 10/2000 |
| EP | 1295941 A1 | 3/2003 |
| JP | 2001-286300 A | 10/2001 |
| JP | 2002-119291 A | 4/2002 |
| WO | 2006/046270 A2 | 5/2006 |
| WO | 2010/045354 A1 | 4/2010 |

OTHER PUBLICATIONS

Tanaka R. et al. Leukemia Research, vol. 32, Issue 9, Sep. 2008, pp. 1462-1467.*
Dvorakova D. et al. Leukemia (2009) 23, 793-796.*
Cazzaniga et al., "Nucleophosmin mutations in childhood acute myelogenous leukemia with normal karyotype," Blood, 106: 1419-1422 (2005).
Dohner et al., "Mutant nucleophosmin (NPM1) predicts favorable prognosis in younger adults with acute myeloid leukemia and normal cytogenetics: interations with other gene mutations," Blood, 106: 3740-3746 (2005).
Falini et al., "Acute myeloid leukemia carrying cytoplasmic/mutated nucleophosmin (NPMc + AML): biologic and clinical features," Blood, 109: 874-885 (2007).
Falini et al., "Cytoplasmic Nucleophosmin in Acute Myelogenous Leukemia with a Normal Karyotype," New England Journal of Medicine, 352: 254-266 (2005).
Falini et al., "Immunohistochemistry predicts nucleophosmin (NPM) mutations in acute myeloid leukemia," Blood, 108: 1999-2005 (2006).
Palmisano et al., "NPM1 mutations are more stable than FLT3 mutations during the course of disease in patients with acute myeloid leukemia," Haematologica, 92: 1268-1269 (2007).
Schnittger et al., "Nucleophosmin gene mutations are predictors of favorable prognosis in acute myelogenous leukemia with a normal karyotype," Blood, 106: 3733-3739 (2005).
Suzuki et al., "Clinical characteristics and prognostics implications of NPM1 mutations in acute myeloid leukemia," Blood, 106: 2854-2861 (2005).
Extended European Search Report issued in European Patent Application No. 12166071.6 dated Aug. 2, 2012.
Laughlin et al., "Rapid Method for Detection of Mutations in the Nucleophosmin Gene in Acute Myeloid Leukemia," Journal of Molecular Diagnostics, 10: 338-345 (2008).
Scholl et al., "Rapid screening and sensitive detection of NPM1 (nucleophosmin) exon 12 mutations in acute myeloid leukaemia," Leukema Research, 31: 1205-1211 (2007).
Tan et al., "Detection of NPM1 exon 12 mutations and FLT3—internal tandem duplications by high resolution melting analysis in normal karyotype acute myeloid leukemia," Journal of Hematology & Oncology, 1: 1-5 (2008).
Chi et al., "Detection of exon 12 type A mutation of NPM1 gene in IMS-M2 cell line," Leukemia Research, 34: 261-262 (2010).
Gorello et al., "Quantitative assessment of minimal residual disease in acute myeloid leukemia carrying nucleophosmin (NPM1) gene mutations," Leukemia, 1-6 (2006).

* cited by examiner

*Primary Examiner* — Stephen Kapushoc
(74) *Attorney, Agent, or Firm* — Morgan, Lewis & Bockius LLP

(57) ABSTRACT

The present invention relates to probes which detect a polymorphism(s) in exon 12 of the NPM1 gene, a kit therefor, and the method of detecting the polymorphism(s) thereof.

13 Claims, 16 Drawing Sheets

Fig. 1
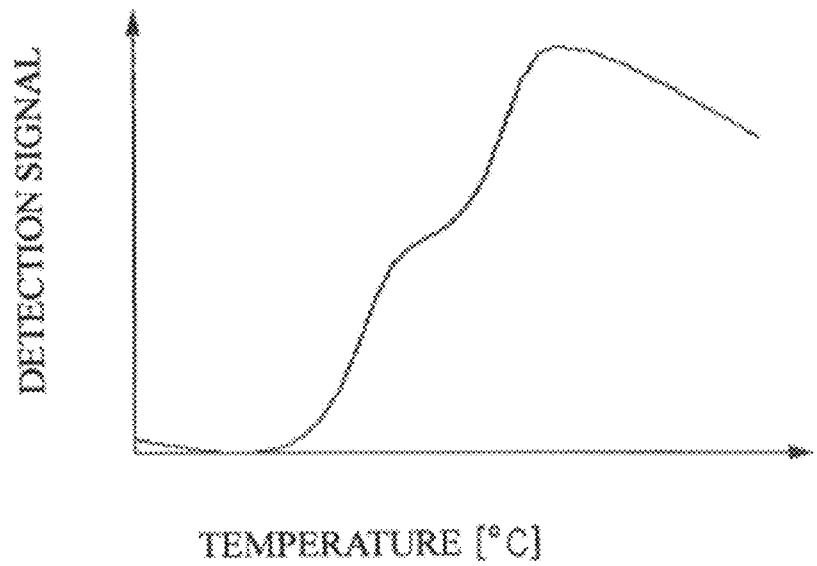
(A)
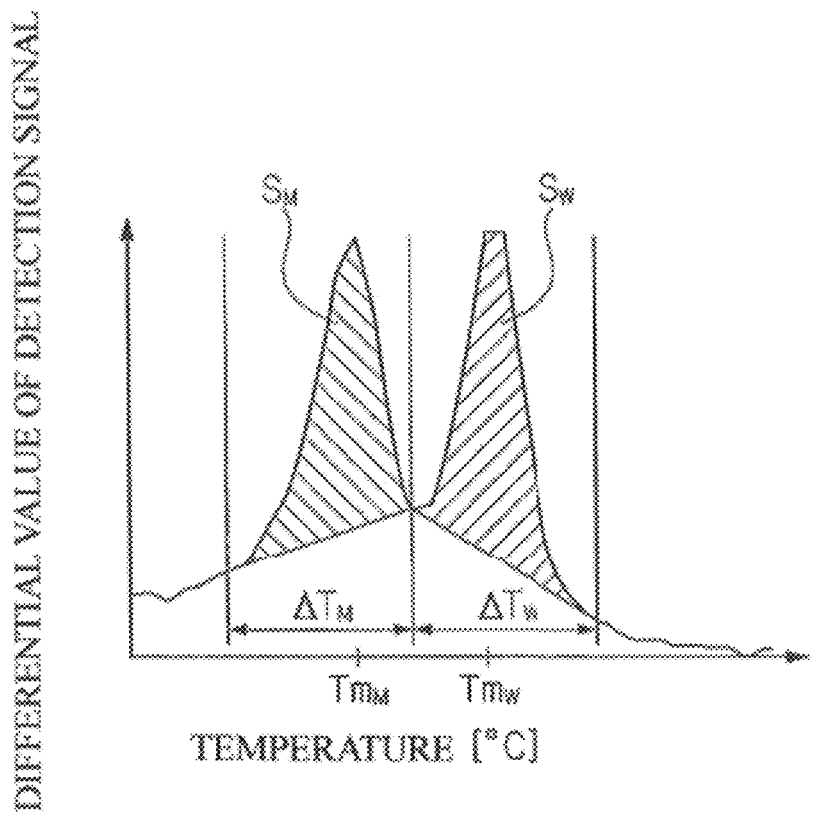
(B)

Fig.3 Schematic View of Design of Probes

SEQUENCE LISTING

```
<160> NUMBER OF SEQ ID NOS: 67

<210> SEQ ID NO 1
<211> LENGTH: 590
<212> TYPE: DNA
<213> ORGANISM: Homo sapiens

<400> SEQUENCE: 1
atatctttat ctagagttaa ctctctggtg gtagaatgaa aaatagatgt tgaactatgc      60
aaagagacat ttaatttatt gatgtctatg aagtgttgtg gttccttaac cacatttctt     120 ttttttttt tccaggctat tcaagatctc tggcagtgga ggaagtctct ttaagaaaat     180
agtttaaaca atttgttaaa aaattttccg tcttatttca tttctgtaac agttgatatc     240
tggctgtcct ttttataatg cagagtgaga actttcccta ccgtgtttga taaatgttgt     300
ccaggttcta ttgccaagaa tgtgttgtcc aaaatgcctg tttagttttt aaagatggaa     360
ctccacccct tgcttggttt taagtatgta tggaatgtta tgataggaca tagtagtagc     420
ggtggtcaga catggaaatg gtggggagac aaaaatatac atgtgaaata aaactcagta     480
ttttaataaa gtagcacggt ttctattgac ttatttaact gctttatact ttgtcaaaga     540
aataattaat gtagttagga atggcaaata gtcttgtaaa attctatgag                590

<210> SEQ ID NO 2
<211> LENGTH: 594
<212> TYPE: DNA
<213> ORGANISM: Homo sapiens

<400> SEQUENCE: 2
```

```
atatctttat ctagagttaa ctctctggtg gtagaatgaa aaatagatgt tgaactatgc    60
aaagagacat ttaatttatt gatgtctatg aagtgttgtg gttccttaac cacatttctt   120
tttttttttt tccaggctat tcaagatctc tgtctggcag tggaggaagt ctctttaaga   180
aaatagttta aacaatttgt taaaaaattt tccgtcttat ttcatttctg taacagttga   240
tatctggctg tccttttat aatgcagagt gagaactttc cctaccgtgt ttgataaatg    300
ttgtccaggt tctattgcca agaatgtgtt gtccaaaatg cctgtttagt ttttaaagat   360
ggaactccac cctttgcttg gttttaagta tgtatggaat gttatgatag gacatagtag   420
tagcggtggt cagacatgga aatggtgggg agacaaaaat atacatgtga aataaaactc   480
agtattttaa taaagtagca cggtttctat tgacttattt aactgcttta tactttgtca   540
aagaaataat taatgtagtt aggaatggca aatagtcttg taaaattcta tgag         594
```

<210> SEQ ID NO 3
<211> LENGTH: 594
<212> TYPE: DNA
<213> ORGANISM: Homo sapiens

<400> SEQUENCE: 3

```
atatctttat ctagagttaa ctctctggtg gtagaatgaa aaatagatgt tgaactatgc    60
aaagagacat ttaatttatt gatgtctatg aagtgttgtg gttccttaac cacatttctt   120
tttttttttt tccaggctat tcaagatctc tggcagtctc ttgcccaagt ctctttaaga   180
aaatagttta aacaatttgt taaaaaattt tccgtcttat ttcatttctg taacagttga   240
tatctggctg tccttttat aatgcagagt gagaactttc cctaccgtgt ttgataaatg    300
ttgtccaggt tctattgcca agaatgtgtt gtccaaaatg cctgtttagt ttttaaagat   360
ggaactccac cctttgcttg gttttaagta tgtatggaat gttatgatag gacatagtag   420
tagcggtggt cagacatgga aatggtgggg agacaaaaat atacatgtga aataaaactc   480
agtattttaa taaagtagca cggtttctat tgacttattt aactgcttta tactttgtca   540
aagaaataat taatgtagtt aggaatggca aatagtcttg taaaattcta tgag         594
```

<210> SEQ ID NO 4
<211> LENGTH: 21
<212> TYPE: DNA
<213> ORGANISM: Artificial Sequence
<220> FEATURE:
<223> OTHER INFORMATION: probe

<400> SEQUENCE: 4

```
tgccagagat cttgaatagc c                                              21
```

<210> SEQ ID NO 5
<211> LENGTH: 27
<212> TYPE: DNA
<213> ORGANISM: Artificial Sequence
<220> FEATURE:
<223> OTHER INFORMATION: probe

<400> SEQUENCE: 5

```
ctattttctt aaagagactt cctccac                                        27
```

<210> SEQ ID NO 6
<211> LENGTH: 54
<212> TYPE: DNA
<213> ORGANISM: Artificial Sequence
<220> FEATURE:
<223> OTHER INFORMATION: oligonucleotide

<400> SEQUENCE: 6
ccaggctatt caagatctct ggcagtggag gaagtctctt taagaaaata gttt          54

<210> SEQ ID NO 7
<211> LENGTH: 58
<212> TYPE: DNA
<213> ORGANISM: Artificial Sequence
<220> FEATURE:
<223> OTHER INFORMATION: oligonucleotide

<400> SEQUENCE: 7
ccaggctatt caagatctct gtctggcagt ggaggaagtc tctttaagaa aatagttt     58

<210> SEQ ID NO 8
<211> LENGTH: 58
<212> TYPE: DNA
<213> ORGANISM: Artificial Sequence
<220> FEATURE:
<223> OTHER INFORMATION: oligonucleotide

<400> SEQUENCE: 8
ccaggctatt caagatctct gcatggcagt ggaggaagtc tctttaagaa aatagttt     58

<210> SEQ ID NO 9
<211> LENGTH: 58
<212> TYPE: DNA
<213> ORGANISM: Artificial Sequence
<220> FEATURE:
<223> OTHER INFORMATION: oligonucleotide

<400> SEQUENCE: 9
ccaggctatt caagatctct gcctggcagt ggaggaagtc tctttaagaa aatagttt     58

<210> SEQ ID NO 10
<211> LENGTH: 58
<212> TYPE: DNA
<213> ORGANISM: Artificial Sequence
<220> FEATURE:
<223> OTHER INFORMATION: oligonucleotide

<400> SEQUENCE: 10
ccaggctatt caagatctat gcctggcagt ggaggaagtc tctttaagaa aatagttt     58

<210> SEQ ID NO 11
<211> LENGTH: 58
<212> TYPE: DNA
<213> ORGANISM: Artificial Sequence
<220> FEATURE:
<223> OTHER INFORMATION: oligonucleotide

<400> SEQUENCE: 11
ccaggctatt caagatctct ggcagaggat ggaggaagtc tctttaagaa aatagttt     58

<210> SEQ ID NO 12
<211> LENGTH: 58
<212> TYPE: DNA
<213> ORGANISM: Artificial Sequence
<220> FEATURE:
<223> OTHER INFORMATION: oligonucleotide

<400> SEQUENCE: 12
ccaggctatt caagatctct ggcagtgctg ctcccaagtc tctttaagaa aatagttt     58

<210> SEQ ID NO 13

```
<211> LENGTH: 58
<212> TYPE: DNA
<213> ORGANISM: Artificial Sequence
<220> FEATURE:
<223> OTHER INFORMATION: oligonucleotide

<400> SEQUENCE: 13
ccaggctatt caagatctct ggcagtctct tgcccaagtc tctttaagaa aatagttt         58

<210> SEQ ID NO 14
<211> LENGTH: 59
<212> TYPE: DNA
<213> ORGANISM: Artificial Sequence
<220> FEATURE:
<223> OTHER INFORMATION: oligonucleotide

<400> SEQUENCE: 14
ccaggctatt caagatctct ggcaagattt cttaaatcgt ctctttaaga aaatagttt        59

<210> SEQ ID NO 15
<211> LENGTH: 25
<212> TYPE: DNA
<213> ORGANISM: Artificial Sequence
<220> FEATURE:
<223> OTHER INFORMATION: probe

<400> SEQUENCE: 15
gagacttcct ccactgccag agatc                                             25

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
gatgtctatg aagtgttgtg gttcct                                            26

<210> SEQ ID NO 17
<211> LENGTH: 31
<212> TYPE: DNA
<213> ORGANISM: Artificial Sequence
<220> FEATURE:
<223> OTHER INFORMATION: primer

<400> SEQUENCE: 17
caactgttac agaaatgaaa taagacggaa a                                      31

<210> SEQ ID NO 18
<211> LENGTH: 56
<212> TYPE: DNA
<213> ORGANISM: Homo sapiens

<400> SEQUENCE: 18
gaccaagagg ctattcaaga tctctggcag tggaggaagt ctctttaaga aaatag           56

<210> SEQ ID NO 19
<211> LENGTH: 60
<212> TYPE: DNA
<213> ORGANISM: Homo sapiens

<400> SEQUENCE: 19
gaccaagagg ctattcaaga tctctgtctg gcagtggagg aagtctcttt aagaaaatag       60
```

```
<210> SEQ ID NO 20
<211> LENGTH: 60
<212> TYPE: DNA
<213> ORGANISM: Homo sapiens

<400> SEQUENCE: 20
gaccaagagg ctattcaaga tctctgcatg gcagtggagg aagtctcttt aagaaaatag    60

<210> SEQ ID NO 21
<211> LENGTH: 60
<212> TYPE: DNA
<213> ORGANISM: Homo sapiens

<400> SEQUENCE: 21
gaccaagagg ctattcaaga tctctgcgtg gcagtggagg aagtctcttt aagaaaatag    60

<210> SEQ ID NO 22
<211> LENGTH: 60
<212> TYPE: DNA
<213> ORGANISM: Homo sapiens

<400> SEQUENCE: 22
gaccaagagg ctattcaaga tctctgcctg gcagtggagg aagtctcttt aagaaaatag    60

<210> SEQ ID NO 23
<211> LENGTH: 60
<212> TYPE: DNA
<213> ORGANISM: Homo sapiens

<400> SEQUENCE: 23
gaccaagagg ctattcaaga tctctggcag tctcttgccc aagtctcttt aagaaaatag    60

<210> SEQ ID NO 24
<211> LENGTH: 60
<212> TYPE: DNA
<213> ORGANISM: Homo sapiens

<400> SEQUENCE: 24
gaccaagagg ctattcaaga tctctggcag tccctggaga aagtctcttt aagaaaatag    60

<210> SEQ ID NO 25
<211> LENGTH: 60
<212> TYPE: DNA
<213> ORGANISM: Homo sapiens

<400> SEQUENCE: 25
gaccaagagg ctattcaaga tctctggcag tccctcgccc aagtctcttt aagaaaatag    60

<210> SEQ ID NO 26
<211> LENGTH: 60
<212> TYPE: DNA
<213> ORGANISM: Homo sapiens

<400> SEQUENCE: 26
gaccaagagg ctattcaaga tctctggcag tgcttcgccc aagtctcttt aagaaaatag    60

<210> SEQ ID NO 27
<211> LENGTH: 60
<212> TYPE: DNA
<213> ORGANISM: Homo sapiens

<400> SEQUENCE: 27
gaccaagagg ctattcaaga tctctggcag tgttttttcaa aagtctcttt aagaaaatag    60
```

<210> SEQ ID NO 28
<211> LENGTH: 60
<212> TYPE: DNA
<213> ORGANISM: Homo sapiens

<400> SEQUENCE: 28
gaccaagagg ctattcaaga tctctggcag tctctttcta aagtctcttt aagaaaatag    60

<210> SEQ ID NO 29
<211> LENGTH: 55
<212> TYPE: DNA
<213> ORGANISM: Homo sapiens

<400> SEQUENCE: 29
gaccaagagg ctattcaaga tctctcccgg gcagtaagtc tctttaagaa aatag    55

<210> SEQ ID NO 30
<211> LENGTH: 60
<212> TYPE: DNA
<213> ORGANISM: Homo sapiens

<400> SEQUENCE: 30
gaccaagagg ctattcaaga tctctggcag tcccttccca aagtctcttt aagaaaatag    60

<210> SEQ ID NO 31
<211> LENGTH: 60
<212> TYPE: DNA
<213> ORGANISM: Homo sapiens

<400> SEQUENCE: 31
gaccaagagg ctattcaaga tctctgtagc gcagtggagg aagtctcttt aagaaaatag    60

<210> SEQ ID NO 32
<211> LENGTH: 59
<212> TYPE: DNA
<213> ORGANISM: Homo sapiens

<400> SEQUENCE: 32
gaccaagagg ctattcaaga tctctccacg cagtggagga agtctcttta agaaaatag    59

<210> SEQ ID NO 33
<211> LENGTH: 62
<212> TYPE: DNA
<213> ORGANISM: Homo sapiens

<400> SEQUENCE: 33
gaccaagagg ctattcaaga tctctggcag cgtttccgga ggaagtctct ttaagaaaat    60
ag    62

<210> SEQ ID NO 34
<211> LENGTH: 60
<212> TYPE: DNA
<213> ORGANISM: Homo sapiens

<400> SEQUENCE: 34
gaccaagagg ctattcaaga tctctgtacc ttcctggagg aagtctcttt aagaaaatag    60

<210> SEQ ID NO 35
<211> LENGTH: 60
<212> TYPE: DNA
<213> ORGANISM: Homo sapiens

<400> SEQUENCE: 35

-continued gaccaagagg ctattcaaga tctctggcag aggatggagg aagtctcttt aagaaaatag    60

<210> SEQ ID NO 36
<211> LENGTH: 60
<212> TYPE: DNA
<213> ORGANISM: Homo sapiens

<400> SEQUENCE: 36
gaccaagagg ctattcaaga tctctgcagg gcagtggagg aagtctcttt aagaaaatag    60

<210> SEQ ID NO 37
<211> LENGTH: 60
<212> TYPE: DNA
<213> ORGANISM: Homo sapiens

<400> SEQUENCE: 37
gaccaagagg ctattcaaga tctctgccgg gcagtggagg aagtctcttt aagaaaatag    60

<210> SEQ ID NO 38
<211> LENGTH: 60
<212> TYPE: DNA
<213> ORGANISM: Homo sapiens

<400> SEQUENCE: 38
gaccaagagg ctattcaaga tctctgccgc ggagtggagg aagtctcttt aagaaaatag    60

<210> SEQ ID NO 39
<211> LENGTH: 60
<212> TYPE: DNA
<213> ORGANISM: Homo sapiens

<400> SEQUENCE: 39
gaccaagagg ctattcaaga tctctgccag gcagtggagg aagtctcttt aagaaaatag    60

<210> SEQ ID NO 40
<211> LENGTH: 60
<212> TYPE: DNA
<213> ORGANISM: Homo sapiens

<400> SEQUENCE: 40
gaccaagagg ctattcaaga tctctgtttg gcagtggagg aagtctcttt aagaaaatag    60

<210> SEQ ID NO 41
<211> LENGTH: 60
<212> TYPE: DNA
<213> ORGANISM: Homo sapiens

<400> SEQUENCE: 41
gaccaagagg ctattcaaga tctctgtcgg gcagtggagg aagtctcttt aagaaaatag    60

<210> SEQ ID NO 42
<211> LENGTH: 60
<212> TYPE: DNA
<213> ORGANISM: Homo sapiens

<400> SEQUENCE: 42
gaccaagagg ctattcaaga tctctggcag tccatggagg aagtctcttt aagaaaatag    60

<210> SEQ ID NO 43
<211> LENGTH: 60
<212> TYPE: DNA
<213> ORGANISM: Homo sapiens

```
<400> SEQUENCE: 43
gaccaagagg ctattcaaga tctctgtcat gcagtggagg aagtctcttt aagaaaatag    60

<210> SEQ ID NO 44
<211> LENGTH: 60
<212> TYPE: DNA
<213> ORGANISM: Homo sapiens

<400> SEQUENCE: 44
gaccaagagg ctattcaaga tctctgcttg gcagtggagg aagtctcttt aagaaaatag    60

<210> SEQ ID NO 45
<211> LENGTH: 61
<212> TYPE: DNA
<213> ORGANISM: Homo sapiens

<400> SEQUENCE: 45
gaccaagagg ctattcaaga tctctggcaa gatttcttaa atcgtctctt taagaaaata    60
g                                                                    61

<210> SEQ ID NO 46
<211> LENGTH: 60
<212> TYPE: DNA
<213> ORGANISM: Homo sapiens

<400> SEQUENCE: 46
gaccaagagg ctattcaaga tctatgcctg gcagtggagg aagtctcttt aagaaaatag    60

<210> SEQ ID NO 47
<211> LENGTH: 60
<212> TYPE: DNA
<213> ORGANISM: Homo sapiens

<400> SEQUENCE: 47
gaccaagagg ctattcaaga tctctggccc gcagtggagg aagtctcttt aagaaaatag    60

<210> SEQ ID NO 48
<211> LENGTH: 60
<212> TYPE: DNA
<213> ORGANISM: Homo sapiens

<400> SEQUENCE: 48
gaccaagagg ctattcaaga tctctgtaag gcagtggagg aagtctcttt aagaaaatag    60

<210> SEQ ID NO 49
<211> LENGTH: 60
<212> TYPE: DNA
<213> ORGANISM: Homo sapiens

<400> SEQUENCE: 49
gaccaagagg ctattcaaga tctctggcag tgctgctccc aagtctcttt aagaaaatag    60

<210> SEQ ID NO 50
<211> LENGTH: 60
<212> TYPE: DNA
<213> ORGANISM: Homo sapiens

<400> SEQUENCE: 50
gaccaagagg ctattcaaga tctctggcag ttattttccc aagtctcttt aagaaaatag    60

<210> SEQ ID NO 51
<211> LENGTH: 60
```

```
<212> TYPE: DNA
<213> ORGANISM: Homo sapiens

<400> SEQUENCE: 51
gaccaagagg ctattcaaga tctctgtttg gcagtggagg aagtctcttt aagaaaatag    60

<210> SEQ ID NO 52
<211> LENGTH: 60
<212> TYPE: DNA
<213> ORGANISM: Homo sapiens

<400> SEQUENCE: 52
gaccaagagg ctattcaaga tctctgcttg gcagtggagg aagtctcttt aagaaaatag    60

<210> SEQ ID NO 53
<211> LENGTH: 60
<212> TYPE: DNA
<213> ORGANISM: Homo sapiens

<400> SEQUENCE: 53
gaccaagagg ctattcaaga tctctgtaag gcagtggagg aagtctcttt aagaaaatag    60

<210> SEQ ID NO 54
<211> LENGTH: 60
<212> TYPE: DNA
<213> ORGANISM: Homo sapiens

<400> SEQUENCE: 54
gaccaagagg ctattcaaga tctctgtatg gcagtggagg aagtctcttt aagaaaatag    60

<210> SEQ ID NO 55
<211> LENGTH: 60
<212> TYPE: DNA
<213> ORGANISM: Homo sapiens

<400> SEQUENCE: 55
gaccaagagg ctattcaaga tctctgcaga gcagtggagg aagtctcttt aagaaaatag    60

<210> SEQ ID NO 56
<211> LENGTH: 18
<212> TYPE: DNA
<213> ORGANISM: Artificial Sequence
<220> FEATURE:
<223> OTHER INFORMATION: probe

<400> SEQUENCE: 56
cactgccaga cagagatc                                                  18

<210> SEQ ID NO 57
<211> LENGTH: 18
<212> TYPE: DNA
<213> ORGANISM: Artificial Sequence
<220> FEATURE:
<223> OTHER INFORMATION: probe

<400> SEQUENCE: 57
cactgccatg cagagatc                                                  18

<210> SEQ ID NO 58
<211> LENGTH: 18
<212> TYPE: DNA
<213> ORGANISM: Artificial Sequence
<220> FEATURE:
<223> OTHER INFORMATION: probe
```

<400> SEQUENCE: 58
cactgccagg cagagatc                                             18

<210> SEQ ID NO 59
<211> LENGTH: 60
<212> TYPE: DNA
<213> ORGANISM: artificial
<220> FEATURE:
<223> OTHER INFORMATION: probe

<400> SEQUENCE: 59
gaccaagagg ctattcaaga tctctgtctg gcagtggagg aagtctcttt aagaaaatag    60

<210> SEQ ID NO 60
<211> LENGTH: 60
<212> TYPE: DNA
<213> ORGANISM: Artificial
<220> FEATURE:
<223> OTHER INFORMATION: probe

<400> SEQUENCE: 60
gaccaagagg ctattcaaga tctctgcatg gcagtggagg aagtctcttt aagaaaatag    60

<210> SEQ ID NO 61
<211> LENGTH: 60
<212> TYPE: DNA
<213> ORGANISM: artificial
<220> FEATURE:
<223> OTHER INFORMATION: probe

<400> SEQUENCE: 61
gaccaagagg ctattcaaga tctctgcctg gcagtggagg aagtctcttt aagaaaatag    60

<210> SEQ ID NO 62
<211> LENGTH: 60
<212> TYPE: DNA
<213> ORGANISM: artificial
<220> FEATURE:
<223> OTHER INFORMATION: probe

<400> SEQUENCE: 62
gaccaagagg ctattcaaga tctatgcctg gcagtggagg aagtctcttt aagaaaatag    60

<210> SEQ ID NO 63
<211> LENGTH: 60
<212> TYPE: DNA
<213> ORGANISM: artificial
<220> FEATURE:
<223> OTHER INFORMATION: probe

<400> SEQUENCE: 63
gaccaagagg ctattcaaga tctctggcag aggatggagg aagtctcttt aagaaaatag    60

<210> SEQ ID NO 64
<211> LENGTH: 60
<212> TYPE: DNA
<213> ORGANISM: artificial
<220> FEATURE:
<223> OTHER INFORMATION: probe

<400> SEQUENCE: 64
gaccaagagg ctattcaaga tctctggcag tgctgctccc aagtctcttt aagaaaatag    60

<210> SEQ ID NO 65
<211> LENGTH: 60

```
<212> TYPE: DNA
<213> ORGANISM: artificial
<220> FEATURE:
<223> OTHER INFORMATION: probe

<400> SEQUENCE: 65
gaccaagagg ctattcaaga tctctggcag tctcttgccc aagtctcttt aagaaaatag      60

<210> SEQ ID NO 66
<211> LENGTH: 61
<212> TYPE: DNA
<213> ORGANISM: artificial
<220> FEATURE:
<223> OTHER INFORMATION: probe

<400> SEQUENCE: 66
gaccaagagg ctattcaaga tctctggcaa gatttcttaa atcgtctctt taagaaaata      60
g                                                                     61

<210> SEQ ID NO 67
<211> LENGTH: 56
<212> TYPE: DNA
<213> ORGANISM: Homo sapiens

<400> SEQUENCE: 67
gaccaagagg ctattcaaga tctctggcag tggaggaagt ctctttaaga aaatag          56
```

US 8,877,910 B2

PROBE FOR DETECTING POLYMORPHISM IN EXON 12 OF NPM1 GENE AND USE THEREOF

CROSS-REFERENCE TO RELATED APPLICATION

This application claims priority from Japanese Patent Application No. 2011-102327 filed on Apr. 28, 2011, the subject matter of which is incorporated herein by reference in its entirety.

SEQUENCE LISTING SUBMISSION VIA EFS-WEB

A computer readable text file, entitled "SequenceListing.txt," created on or about May 1, 2014 with a file size of about 2 kb contains the sequence listing for this application and is hereby incorporated by reference in its entirety.

TECHNICAL FIELD

The present invention relates to probes which detect a polymorphism(s) in exon 12 of the NPM1 gene, a kit therefor, and the method of detecting the polymorphism(s) thereof.

Many DNA mutations involved in causes of acute myeloid leukemia (AML) have been discovered so far. Mutations of the NPM1 gene are found in adult patients suffering from acute myeloid leukemia, and it has been reported that these can be used for prognosis prediction by taking those mutations into consideration in combination with the result of analysis of the FLT3-ITD gene mutation (Blood. 2007, 109: 874-885). Examples of the type of mutation of the NPM1 gene include those described in New Eng J Med 352: 254-266, 2005; Blood 106: 1419-1422, 2005; Blood 106: 3740-3746, 2005; Blood 106: 3733-3739, 2005; Blood 108: 1999-2005, 2005; and Blood 106: 2854-2861, 2005, and representative examples of the mutations include Type A, Type, B, Type D, Type 7, Type Q, Type 10, Type E and Type 6 in view of the number of cases reported and the positions in nucleotide sequences where the mutations occur.

Blood 106: 2854-2861, 2005 describes a method wherein amplification by PCR is carried out and the resulting amplification product is separated by electrophoresis, followed by cutting out a part of the gel, purifying the amplification product from the gel and subjecting the purified product to direct sequencing. Haematologica 92: 1268-1269, 2007 describes a method by detection using the DHPLC method and the sequencing method.

However, in these methods, (1) since an amplification product needs to be recovered, there is the risk of contamination; (2) since the operations are not automated, and since each step requires an operation, the methods are laborious and costly; (3) special knowledge and special skills are required for analysis of results; and (4) since the detection specificity in sequencing analysis is as low as about 20%, detection is difficult when the ratio of normal cells contained together with cancer cells is high; which are problematic.

On the other hand, methods wherein a region containing a mutation is amplified by PCR and a fluorescently labeled nucleic acid probe is used to carry out melting curve analysis, followed by analyzing the mutation based on the result of the melting curve analysis have been described (JP 2001-286300 A and JP 2002-119291 A). In these literatures, a probe is designed such that, when a quenching probe labeled at its end with a fluorescent dye is hybridized with a target nucleic acid, a plurality of base pairs of the probe-nucleic acid hybrid form at least one GC pair at the end portion. However, these methods had a problem in that the methods are not necessarily applicable to an arbitrary sequence.

SUMMARY OF THE INVENTION

The present invention aims to specify probes effective for detecting mutations in exon 12 of the NPM1 gene and to provide a method for detecting the mutations in exon 12 of the NPM1 gene and a kit therefor.

The present inventors discovered that, by designing probes based on specific regions containing mutations in exon 12 of the NPM1 gene and carrying out melting curve analysis using the probes, the mutations can be detected, thereby completing the present invention.

That is, the present invention in one aspect includes a labeled probe comprising at least one oligonucleotide selected from the group consisting of oligonucleotides P5, P6, P7, P1, and P2:

(P5) an oligonucleotide comprising a sequence at least about 85% identical to a complementary nucleotide sequence of 12 to 50 nucleotides to nucleotides 145 to 156 of SEQ ID NO:2;

(P6) an oligonucleotide comprising a sequence at least about 85% identical to a complementary nucleotide sequence of 12 to 50 nucleotides to nucleotides 145 to 156 of SEQ ID NO:2, wherein the nucleotide corresponding to the nucleotide at position 153 is guanine;

(P7) an oligonucleotide comprising a sequence at least about 85% identical to a complementary nucleotide sequence of 12 to 50 nucleotides to nucleotides 145 to 156 of SEQ ID NO:2, wherein the nucleotide corresponding to the nucleotide at position 153 is guanine, and the nucleotide corresponding to the nucleotide at position 154 is thymine;

(P1) an oligonucleotide comprising a sequence at least about 85% identical to a complementary nucleotide sequence of 16 to 50 nucleotides to nucleotides 135 to 150 of SEQ ID NO:1; and (P2) an oligonucleotide comprising a sequence at least about 85% identical to a complementary nucleotide sequence of 19 to 50 nucleotides to nucleotides 164 to 182 of SEQ ID NO:1.

In some embodiments, said oligonucleotide (P5) comprises a complementary nucleotide sequence of 12 to 50 nucleotides to nucleotides 145 to 156 of SEQ ID NO:2; said oligonucleotide (P6) comprises a complementary nucleotide sequence of 12 to 50 nucleotides to nucleotides 145 to 156 of SEQ ID NO:2, wherein the nucleotide corresponding to the nucleotide at position 153 is guanine; said oligonucleotide (P7) comprises a complementary nucleotide sequence of 12 to 50 nucleotides to nucleotides 145 to 156 of SEQ ID NO:2, wherein the nucleotide corresponding to the nucleotide at position 153 is guanine, and the nucleotide corresponding to the nucleotide at position 154 is thymine; said oligonucleotide (P1) comprises a complementary nucleotide sequence of 16 to 50 nucleotides to nucleotides 135 to 150 of SEQ ID NO:1; and said oligonucleotide (P2) comprises a complementary nucleotide sequence of 19 to 50 nucleotides to nucleotides 164 to 182 of SEQ ID NO:1.

The present invention in another aspect includes probes which detect for a mutation(s) in exon 12 of the NPM1 gene, comprising at least one of fluorescently labeled oligonucleotide selected from the group consisting of P5, P5', P6, P6', P7, P7', P1, P1', P2 and P2' below:

(P5) an oligonucleotide comprising a nucleotide sequence complementary to a nucleotide sequence of 12 to 50 consecutive nucleotides containing nucleotides 145 to 156 in SEQ ID NO:2 or a homologous sequence thereof, wherein the nucleotide corresponding to the nucleotide at position 145 is cytosine labeled with a fluorescent dye;

(P5') an oligonucleotide comprising a nucleotide sequence complementary to a nucleotide sequence of 12 to 50 consecutive nucleotides containing nucleotides 145 to 156 in SEQ ID NO:2 or a sequence which hybridizes with the nucleotide sequence in SEQ ID NO:2 under stringent conditions, wherein the nucleotide corresponding to the nucleotide at position 145 is cytosine labeled with a fluorescent dye;

(P6) an oligonucleotide comprising a nucleotide sequence complementary to a nucleotide sequence of 12 to 50 consecutive nucleotides containing nucleotides 145 to 156 in SEQ ID NO:2 or a homologous sequence thereof, wherein the nucleotide corresponding to the nucleotide at position 145 is cytosine labeled with a fluorescent dye and the nucleotide corresponding to the nucleotide at position 153 is guanine;

(P6') an oligonucleotide comprising a nucleotide sequence complementary to a nucleotide sequence of 12 to 50 consecutive nucleotides containing nucleotides 145 to 156 in SEQ ID NO:2 or a sequence which hybridizes with the nucleotide sequence in SEQ ID NO:2 under stringent conditions, wherein the nucleotide corresponding to the nucleotide at position 145 is cytosine labeled with a fluorescent dye and the nucleotide corresponding to the nucleotide at position 153 is guanine;

(P7) an oligonucleotide comprising a nucleotide sequence complementary to a nucleotide sequence of 12 to 50 consecutive nucleotides containing nucleotides 145 to 156 in SEQ ID NO:2 or a homologous sequence thereof, wherein the nucleotide corresponding to the nucleotide at position 145 is cytosine labeled with a fluorescent dye, the nucleotide corresponding to the nucleotide at position 153 is guanine, and the nucleotide corresponding to the nucleotide at position 154 is thymine;

(P7') an oligonucleotide comprising a nucleotide sequence complementary to a nucleotide sequence of 12 to 50 consecutive nucleotides containing nucleotides 145 to 156 in SEQ ID NO:2 or a sequence which hybridizes with the nucleotide sequence in SEQ ID NO:2 under stringent conditions, wherein the nucleotide corresponding to the nucleotide at position 145 is cytosine labeled with a fluorescent dye, the nucleotide corresponding to the nucleotide at position 153 is guanine, and the nucleotide corresponding to the nucleotide at position 154 is thymine;

(P1) an oligonucleotide comprising a nucleotide sequence complementary to a nucleotide sequence of 16 to 50 consecutive nucleotides containing nucleotides 135 to 150 in SEQ ID NO:1 or a homologous sequence thereof, wherein the nucleotide corresponding to the nucleotide at position 135 is cytosine labeled with a fluorescent dye;

(P1') an oligonucleotide comprising a nucleotide sequence complementary to a nucleotide sequence of 16 to 50 consecutive nucleotides containing nucleotides 135 to 150 in SEQ ID NO:1 or a sequence which hybridizes with the nucleotide sequence in SEQ ID NO:1 under stringent conditions, wherein the nucleotide at position 135 is cytosine labeled with a fluorescent dye;

(P2) an oligonucleotide comprising a nucleotide sequence complementary to a nucleotide sequence of 19 to 50 consecutive nucleotides containing nucleotides 164 to 182 in SEQ ID NO:1 or a homologous sequence thereof, wherein the nucleotide corresponding to the nucleotide at position 182 is cytosine labeled with a fluorescent dye; and (P2') an oligonucleotide comprising a nucleotide sequence complementary to a nucleotide sequence of 19 to 50 consecutive nucleotides containing nucleotides 164 to 182 in SEQ ID NO:1 or a sequence which hybridizes with the nucleotide sequence in SEQ ID NO:1 under stringent conditions, wherein the nucleotide corresponding to the nucleotide at position 182 is cytosine labeled with a fluorescent dye.

In another aspect, oligonucleotides P5, P5', P6, P6', P7, and P7' described herein have the nucleotide corresponding to the nucleotide at position 145 labeled with a fluorescent dye at the first, second or third position from the 3' end; oligonucleotides P1 and P1' described herein have the nucleotide corresponding to the nucleotide at position 135 labeled with a fluorescent dye at the first, second or third position from the 3' end; and oligonucleotides P2 and P2' described herein have the nucleotide corresponding to the nucleotide at position 182 labeled with a fluorescent dye at the first, second or third position from the 5' end.

In yet another aspect, oligonucleotides P5, P5', P6, P6', P7, and P7' described herein have the nucleotide corresponding to the nucleotide at position 145 labeled with a fluorescent dye at the 3' end; oligonucleotides P1 and P1' described herein have the nucleotide corresponding to the nucleotide at position 135 labeled with a fluorescent dye at the 3' end; and oligonucleotides P2 and P2' described herein have the base corresponding to the nucleotide at position 182 labeled with a fluorescent dye at the 5' end.

In additional embodiments, oligonucleotides P1 and P1' described herein have the nucleotide corresponding to any one of the nucleotides at positions 153 to 156 at the 5' end and the nucleotides corresponding to the nucleotide at position 135 labeled with a fluorescent dye at the 3' end; and oligonucleotides P2 and P2' described herein have the nucleotide corresponding to any one of the nucleotides at positions 153 to 156 at the 3' end and the nucleotide corresponding to the nucleotide at position 182 labeled with a fluorescent dye at the 5' end.

In yet additional embodiments, oligonucleotides P5, P5', P6, P6', P7, and P7' described herein have the nucleotide corresponding to the nucleotide at position 162 at the 5' end and the nucleotide corresponding to the nucleotide at position 145 labeled with a fluorescent dye at the 3' end; oligonucleotides P1 and P1' described herein have the nucleotide corresponding to the nucleotide at position 155 at the 5' end and the nucleotide corresponding to the nucleotide at position 135 labeled with a fluorescent dye at the 3' end; and oligonucleotides P2 and P2' described herein have the nucleotide corresponding to the nucleotide at position 156 at the 3' end and the nucleotide corresponding to the nucleotide at position 182 labeled with a fluorescent dye at the 5' end.

In further embodiments, oligonucleotides described herein emit fluorescence when probe is not hybridized with a target sequence and the fluorescence intensity decreases or increases when probe is hybridized with target sequence.

In yet further embodiments, oligonucleotides described herein emit fluorescence when probe described herein is not hybridized with a target sequence and the fluorescence intensity decreases when probe is hybridized with the target sequence.

In one aspect, the probe described herein is a probe for melting curve analysis.

In another aspect, oligonucleotides P5, P5', P6, P6', P7, and P7' described herein have 12 to 35 consecutive nucleotides, oligonucleotides P1 and P1' have 16 to 35 consecutive nucleotides, and oligonucleotides P2 and P2' have 19 to 35 consecutive nucleotides.

The present invention also includes a method for detecting a polymorphism(s) in exon 12 of the NPM1 gene, which method uses a probe described herein.

In one aspect, the method includes (I) adding the probe described herein to a sample comprising nucleic acid, to allow said probe to hybridize with said nucleic acid;

(II) changing the temperature to dissociate the hybrid-forming body between said nucleic acid and said probe, and measuring fluctuation of a signal due to the dissociation of said hybrid-forming body;

(III) analyzing said fluctuation of a signal to detect the Tm value of single-stranded nucleic acid in said sample; and (IV) determining based on said Tm value the presence or absence of said polymorphism(s) of interest or the abundance ratio(s) of single-stranded nucleic acid having said polymorphism(s) in single-stranded nucleic acid in said sample.

In another aspect, the method further comprising amplifying DNA before Step (I) or at the same time with Step (I).

The present invention also includes a method for analyzing the risk of developing acute myeloid leukemia, and/or the diseased state and/or prognosis of acute myeloid leukemia by using the methods described herein, comprising detecting a polymorphism(s) in exon 12 of the NPM1 gene and determining the presence/absence of the polymorphism(s).

The present invention further includes a reagent kit which detects a polymorphism(s) in the NPM1 gene, comprising the probe described herein.

In one aspect, the reagent kit comprises primers for amplifying a region(s) comprising a sequence(s) in the nucleotide sequence shown in SEQ ID NO:1 in the NPM1 gene, with which oligonucleotide(s) P5, P5', P6, P6', P7, P7', P1, P1', P2 and/or P2' hybridize(s).

In another aspect, said primers are for detecting a polymorphism(s), selected from P3 and P4, or P3' and P4':

(P3) an oligonucleotide of 10 to 50 consecutive nucleotides having T at position 106 at the 3' end, which is homologous to SEQ ID NO:1; and (P4) an oligonucleotide of 10 to 50 consecutive nucleotides having T at position 205 at the 3' end, which is homologous to the complementary strand of SEQ ID NO:1; or (P3') an oligonucleotide of 10 to 50 consecutive nucleotides having T at position 106 at the 3' end, which hybridizes with the complementary strand of SEQ ID NO:1 under stringent conditions; and (P4') an oligonucleotide of 10 to 50 consecutive nucleotides having T at 205 position at the 3' end, which hybridizes with the nucleotide sequence of SEQ ID NO:1 under stringent conditions.

Only by adding a probe of the present invention and carrying out melting curve analysis (Tm analysis), a polymorphism(s) in exon 12 of the NPM1 gene can be detected. The probes of the present invention have high specificity and high detection sensitivity. Since, by using the method of the present invention, the operation of recovery of an amplification product can be eliminated even in cases where PCR is carried out, there is hardly the risk of contamination. Further, since the operations in the method of the present invention are simple, they can be easily automated. By using the probes of the present invention, at least 7 mutations can be identified among the 8 representative types of mutations which have been reported so far. Further, 2 representative mutant types (Types A and E) can be detected even in cases where each of these mutations exists in a proportion of as low as about 10% of the wild type.

BRIEF DESCRIPTION OF THE DRAWINGS

FIG. 1 shows diagrams showing examples of (A) a melting curve of a nuclear acid mixture and (B) a differential melting curve.

DESCRIPTION OF EMBODIMENTS

Figure 2:
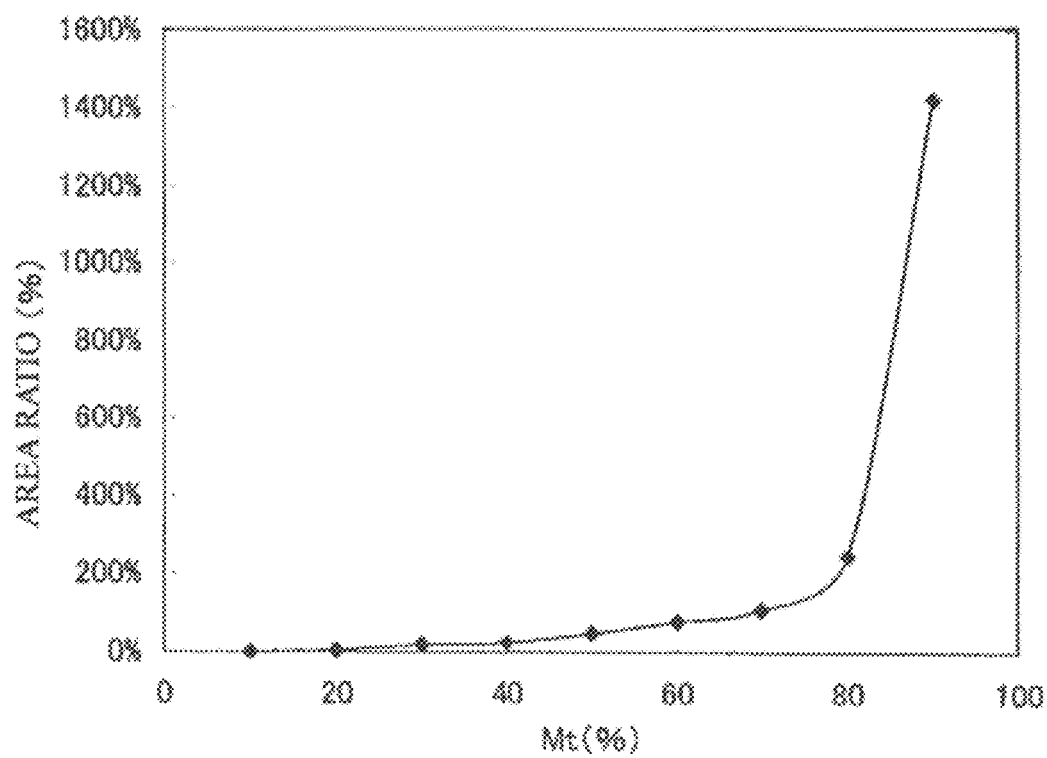
FIG. 2 is a diagram showing an example of a calibration curve.

<1> Probe of Present Invention and Detection Method of Present Invention

The probe according to some embodiments of the present invention is a labeled probe, comprising at least one of oligonucleotide selected from the group consisting of oligonucleotides (P5), (P5'), (P6), (P6'), (P7), (P7'), (P1), (P1'), (P2) and (P2') described herein. In one aspect, the probes are for detecting a polymorphism(s) in exon 12 of the NPM1 gene. In another aspect, the probes are fluorescently labeled.

The oligonucleotide (P5) may comprise a nucleotide sequence complementary to a nucleotide sequence of 12 to 50 consecutive nucleotides containing nucleotides 145 to 156 in SEQ ID NO:2 or a homologous sequence thereof, wherein the nucleotide corresponding to the nucleotide at position 145 is cytosine labeled with a fluorescent dye.

The oligonucleotide (P5') may comprise a nucleotide sequence complementary to a nucleotide sequence of 12 to 50 consecutive nucleotides containing nucleotides 145 to 156 in SEQ ID NO:2 or a sequence which hybridizes with the nucleotide sequence in SEQ ID NO:2 under stringent conditions, wherein the nucleotide corresponding to the nucleotide at position 145 is cytosine labeled with a fluorescent dye.

The oligonucleotide (P6) may comprise a nucleotide sequence complementary to a nucleotide sequence of 12 to 50 consecutive nucleotides containing nucleotides 145 to 156 in SEQ ID NO:2 or a homologous sequence thereof, wherein the nucleotide corresponding to the nucleotide at position 145 is cytosine labeled with a fluorescent dye and the nucleotide corresponding to the nucleotide at position 153 is guanine.

The oligonucleotide (P6') may comprise a nucleotide sequence complementary to a nucleotide sequence of 12 to 50 consecutive nucleotides containing nucleotides 145 to 156 in SEQ ID NO:2 or a sequence which hybridizes with the nucleotide sequence in SEQ ID NO:2 under stringent conditions, wherein the nucleotide corresponding to the nucleotide at position 145 is cytosine labeled with a fluorescent dye and the nucleotide corresponding to the nucleotide at position 153 is guanine.

The oligonucleotide (P7) may comprise a nucleotide sequence complementary to a nucleotide sequence of 12 to 50 consecutive nucleotides containing nucleotides 145 to 156 in SEQ ID NO:2 or a homologous sequence thereof, wherein the nucleotide corresponding to the nucleotide at position 145 is cytosine labeled with a fluorescent dye, the nucleotide corresponding to the nucleotide at position 153 is guanine, and the nucleotide corresponding to the nucleotide at position 154 is thymine.

The oligonucleotide (P7') may comprise a nucleotide sequence complementary to a nucleotide sequence of 12 to 50 consecutive nucleotides containing nucleotides 145 to 156 in SEQ ID NO:2 or a sequence which hybridizes with the nucleotide sequence in SEQ ID NO:2 under stringent conditions, wherein the nucleotide corresponding to the nucleotide at position 145 is cytosine labeled with a fluorescent dye, the nucleotide corresponding to the nucleotide at position 153 is guanine, and the nucleotide corresponding to the nucleotide at position 154 is thymine The oligonucleotide (P1) may comprise a nucleotide sequence complementary to a nucleotide sequence of 16 to 50 consecutive nucleotides containing nucleotides 135 to 150 in SEQ ID NO:1 or a homologous sequence thereof, wherein the nucleotide corresponding to the nucleotide at position 135 is cytosine labeled with a fluorescent dye.

The oligonucleotide (P1') may comprise a nucleotide sequence complementary to a nucleotide sequence of 16 to 50 consecutive nucleotides containing nucleotides 135 to 150 in SEQ ID NO:1 or a sequence which hybridizes with the nucleotide sequence in SEQ ID NO:1 under stringent conditions, wherein the nucleotide at position 135 is cytosine labeled with a fluorescent dye.

The oligonucleotide (P2) may comprise a nucleotide sequence complementary to a nucleotide sequence of 19 to 50 consecutive nucleotides containing nucleotides 164 to 182 in SEQ ID NO:1 or a homologous sequence thereof, wherein the nucleotide corresponding to the nucleotide at position 182 is cytosine labeled with a fluorescent dye.

The oligonucleotide (P2') may comprise a nucleotide sequence complementary to a nucleotide sequence of 19 to 50 consecutive nucleotides containing nucleotides 164 to 182 in SEQ ID NO:1 or a sequence which hybridizes with the nucleotide sequence in SEQ ID NO:1 under stringent conditions, wherein the nucleotide corresponding to the nucleotide at position 182 is cytosine labeled with a fluorescent dye.

In additional embodiments, the oligonucleotide (P5) may comprise or consists of a sequence at least about 85%, 86%, 87%, 88%, 89%, 90%, 91%, 92%, 93%, 94%, 95%, 96%, 97%, 98%, 99%, or 100% identical to a complementary nucleotide sequence of 12 to 50 nucleotides to nucleotides 145 to 156 of SEQ ID NO:2; the oligonucleotide (P6) may comprise or consists of a sequence at least about 85%, 86%, 87%, 88%, 89%, 90%, 91%, 92%, 93%, 94%, 95%, 96%, 97%, 98%, 99%, or 100% identical to a complementary nucleotide sequence of 12 to 50 nucleotides to nucleotides 145 to 156 of SEQ ID NO:2, wherein the nucleotide corresponding to the nucleotide at position 153 is guanine; the oligonucleotide (P7) may comprise or consists of a sequence at least about 85%, 86%, 87%, 88%, 89%, 90%, 91%, 92%, 93%, 94%, 95%, 96%, 97%, 98%, 99%, or 100% identical to a complementary nucleotide sequence of 12 to 50 nucleotides to nucleotides 145 to 156 of SEQ ID NO:2, wherein the nucleotide corresponding to the nucleotide at position 153 is guanine, and the nucleotide corresponding to the nucleotide at position 154 is thymine; the oligonucleotide (P1) may comprise or consists of a sequence at least about 85%, 86%, 87%, 88%, 89%, 90%, 91%, 92%, 93%, 94%, 95%, 96%, 97%, 98%, 99%, or 100% identical to a complementary nucleotide sequence of 16 to 50 nucleotides to nucleotides 135 to 150 of SEQ ID NO:1; and the oligonucleotide (P2) may comprise or consists of a sequence at least about 85%, 86%, 87%, 88%, 89%, 90%, 91%, 92%, 93%, 94%, 95%, 96%, 97%, 98%, 99%, or 100% identical to a complementary nucleotide sequence of 19 to 50 nucleotides to nucleotides 164 to 182 of SEQ ID NO:1.

In some embodiments, said oligonucleotide (P5) comprises a complementary nucleotide sequence of 12 to 50 nucleotides to nucleotides 145 to 156 of SEQ ID NO:2; said oligonucleotide (P6) comprises a complementary nucleotide sequence of 12 to 50 nucleotides to nucleotides 145 to 156 of SEQ ID NO:2, wherein the nucleotide corresponding to the nucleotide at position 153 is guanine; said oligonucleotide (P7) comprises a complementary nucleotide sequence of 12 to 50 nucleotides to nucleotides 145 to 156 of SEQ ID NO:2, wherein the nucleotide corresponding to the nucleotide at position 153 is guanine, and the nucleotide corresponding to the nucleotide at position 154 is thymine; said oligonucleotide (P1) comprises a complementary nucleotide sequence of 16 to 50 nucleotides to nucleotides 135 to 150 of SEQ ID NO:1; and said oligonucleotide (P2) comprises a complementary nucleotide sequence of 19 to 50 nucleotides to nucleotides 164 to 182 of SEQ ID NO:1.

The probes described herein may be prepared in the similar manner described in JP 2001-286300 A and JP 2002-119291 A. Further, the probes described herein also may be prepared in the similar manner as described in JP 2001-286300 A and JP 2002-119291 A. The sequence shown in SEQ ID NO:1 in the present invention corresponds to nucleotides 27689 to 28278 in GenBank accession number NG 016018. SEQ ID NO:2 and SEQ ID NO:1 are the same except that four nucleotides at nucleotides 153-156 are added in SEQ ID NO:2.

The length of the probes P5, P5', P6, P6', P7, and P7' according to one aspect of the present invention is, for example, 12 to 50 consecutive nucleotides, 12 to 35 consecutive nucleotides, or 12 to 30 consecutive nucleotides. The length of the probes P1 and P1' according to another aspect of the present invention is, for example, 16 to 50 consecutive nucleotides, 16 to 35 consecutive nucleotides, or 16 to 30 consecutive nucleotides. The length of the probes P2 and P2' according to another aspect of the present invention is, for example, 19 to 50 consecutive nucleotides, 19 to 35 consecutive nucleotides, or 19 to 30 consecutive nucleotides.

For example, the probe P5, P5', P6, P6', P7, and P7' of the present invention may be a probe having at its 5' end the nucleotide corresponding to any of the nucleotides 160 to 163 in the nucleotide sequence shown in SEQ ID NO:2, or having the nucleotide at position 162 at its 5' end and the nucleotide at position 145 at its 3' end.

For example, the probe of the present invention may be a probe having at its end the nucleotide corresponding to any of the nucleotides 153 to 156 (gcag in Table 1 below) in the nucleotide sequence shown in SEQ ID NO:1, and P1 and P1' has at its 5' end any of the nucleotides at positions 153 to 156 and P2 and P2' has at its 3' end any of the nucleotides at positions 153 to 156. For example, in the probe according to some embodiments of the present invention, P1 and P1' has at its 5' end the nucleotide at position 155 in the nucleotide sequence shown in SEQ ID NO:1 and P2 and P2' has at its 3' end the nucleotide at position 156 in the nucleotide sequence shown in SEQ ID NO:1.

The term "homologous sequence" or "identical sequence" herein means that a nucleotide sequence comprises a sequence having an identity of 80%, 85%, 86%, 87%, 88%, 89%, 90%, 91%, 92%, 93%, 94%, 95%, 96%, 97%, 98% or 99% to the complementary strand of a particular nucleotide sequence. In the present invention, 100% identity may be included.

The hybridization herein can be carried out according to a known method or a method corresponding thereto, such as the method described in Molecular Cloning 3rd (J. Sambrook et al., Cold Spring Harbor Lab. Press, 2001). This literature is hereby incorporated in the present specification by reference.

The stringent conditions mean conditions under which a specific hybrid is formed while nonspecific hybrids are not formed. Typical examples of the stringent conditions include conditions under which hybridization is performed with a potassium concentration of about 25 mM to about 50 mM and a magnesium concentration of about 1.0 mM to about 5.0 mM. Examples of the conditions in the present invention include conditions under which hybridization is performed in Tris-HCl (pH 8.6), 25 mM KCl and 1.5 mM $MgCl_2$, but the conditions are not limited thereto. Other examples of the stringent conditions include those described in Molecular Cloning 3rd (J. Sambrook et al., Cold Spring Harbor Lab. Press, 2001). This literature is hereby incorporated in the present specification by reference. Those skilled in the art can easily select such conditions by controlling the hybridization reaction and/or changing the salt conditions of the hybridization reaction solution.

The labeled oligonucleotides P5, P5', P6, P6', P7, P7', P1, P1', P2 and P2' according to one aspect of the present invention includes labeled oligonucleotides P5, P5', P6, P6', P7, P7', P1, P1', P2 and P2' with one or more nucleotides added, deleted, or substituted, respectively.

The present invention according to one aspect includes the labeled oligonucleotides P5, P5', P6, P6', P7, P7', P1, P1', P2 and P2' with one or more nucleotides added, deleted, or substituted can show the same effect with the labeled oligonucleotides P5, P5', P6, P6', P7, P7', P1, P1', P2 and P2', those oligonucleotides. When nucleotides are added, deleted, or substituted, the position of addition, deletion, or substitution is not particularly limited. The number of nucleotide to be added, deleted, or substituted is one or two nucleotides, for example. Although the number differs according to the whole length of the fluorescently labeled oligonucleotide, the number of nucleotide to be added, deleted, or substituted is 1 to 10, or 1 to 5, for example.

Among the addition, deletion, or substitution, the labeled oligonucleotides P5, P5', P6, P6', P7, P7', P1, P1', P2 and P2' described herein include labeled oligonucleotides P5, P5', P6, P6', P7, P7', P1, P1', P2 and P2' wherein nucleotides in the labeled oligonucleotide(s) are substituted. The position to be substituted is not particularly limited. For example, in view of detection sensitivity, the nucleotides corresponding to nucleotides other than nucleotides 152 to 166 in the nucleotide sequence of SEQ ID NO:2 and nucleotides 152 to 162 in the nucleotide sequence of SEQ ID NO:1 may be substituted. For example, the number of nucleotides to be substituted is 1, 2 or more. Although the number of nucleotides to be substituted depends from the whole number of the labeled oligonucleotide, the number is 1 to 5 nucleotides or 1 to 3 nucleotides, for example.

Oligonucleotides described herein may include modified oligonucleotides. As a unit of the oligonucleotides, ribonucleotides, deoxylibonucleotides, and artificial nucleic acids may be included. The artificial nucleic acids may include DNA, RNA, RNA analogue LNA (Locked Nucleic Acid); PNA (Peptide Nucleic Acid); BNA (Bridged Nucleic Acid) etc. The above-mentioned oligonucleotides may be comprised of one or more kinds of the units.

Examples of the nucleotide sequence of the probe for detection of a mutation(s) in exon 12 of the NPM1 gene used in the present invention include, as P5, 5'-cactgcCAGAcagagatc-3' (SEQ ID NO:56), as P6, 5'-cactgcCATGcagagatc-3' (SEQ ID NO:57), as P7, 5'-cactgcCAGGcagagatc-3' (SEQ ID NO:58), as P1, 5'-tgccagagatcttgaatagcc-3' (SEQ ID NO:4), and, as P2, 5'-ctattttcttaaagagacttcctccac-3' (SEQ ID NO:5).

As the fluorescent dye, those described in JP 2001-286300 A and JP 2002-119291 A may be used, and specific examples of the fluorescent dye include PACIFIC BLUE (trademark), FAM (trademark), TAMRA (trademark) and BODIPY FL (trademark). Examples of the method for binding the fluorescent dye to the oligonucleotide include conventional methods such as the methods described in JP 2001-286300 A and JP 2002-119291 A.

Figure 3:
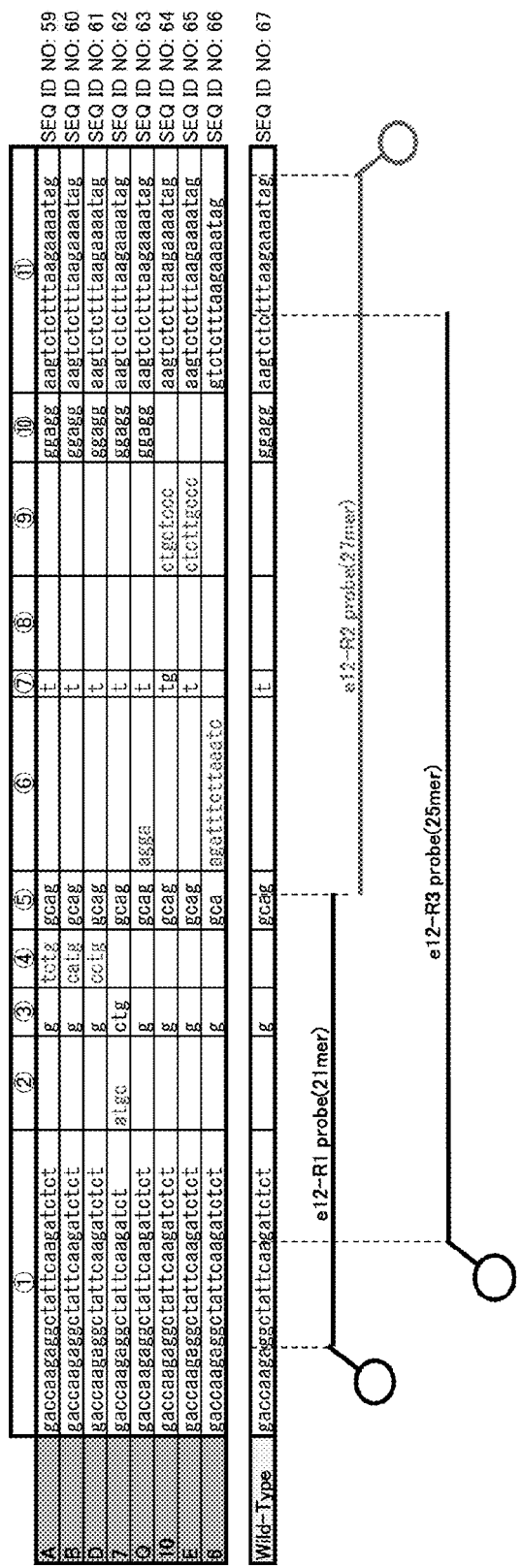
FIG. 3 is a schematic view of the design of the probes of the present invention. The positions of the probes used in Examples are shown. The positions of the probes used in Comparative Examples are also shown.
Figure 4:
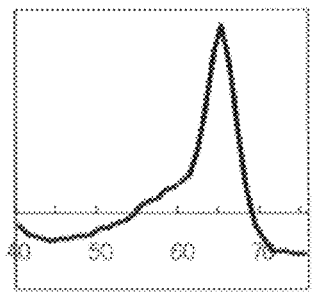
FIG. 4 is a diagram showing the relationship between the amount of change in the fluorescence intensity of TAMRA (3T-NPM1-e12-R1) per unit time (d the amount of increase in the fluorescence intensity/t) and the temperature in the Tm analysis in Example 1 for WT (complementary strand oligonucleotide). The amount of change in the fluorescence intensity per unit time is plotted along the ordinate and the temperature is plotted along the abscissa. This relationship between the ordinate and the abscissa also applies to the diagrams below.
Figure 5:
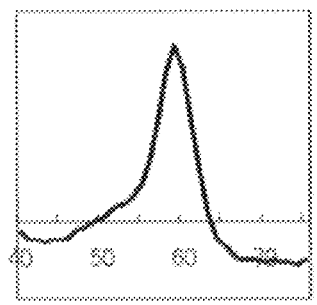
FIG. 5 shows the result of Tm analysis for mutant (mt) type A (complementary strand oligonucleotide) in Example 1 using TAMRA(3T-NPM1-e12-R1) as a probe.
Figure 6:
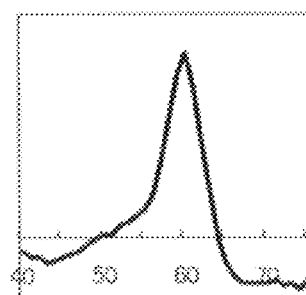
FIG. 6 shows the result of Tm analysis for mt type B (complementary strand oligonucleotide) in Example 1 using TAMRA(3T-NPM1-e12-R1) as a probe.
Figure 7:
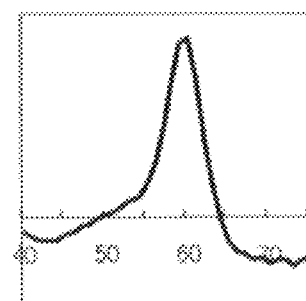
FIG. 7 shows the result of Tm analysis for mt type D (complementary strand oligonucleotide) in Example 1 using TAMRA(3T-NPM1-e12-R1) as a probe.
Figure 8:
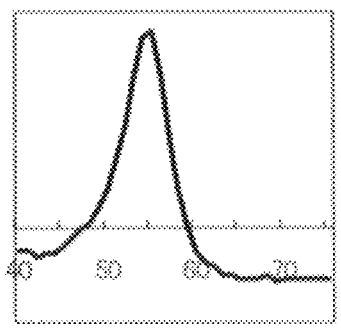
FIG. 8 shows the result of Tm analysis for mt type 7 (complementary strand oligonucleotide) in Example 1 using TAMRA(3T-NPM1-e12-R1) as a probe.
Figure 9:
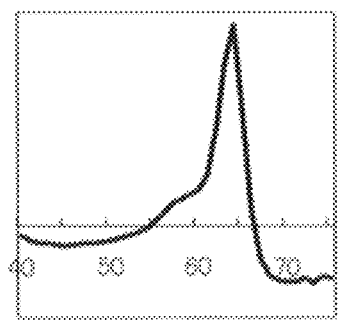
FIG. 9 shows the result of Tm analysis for wild type (WT) (complementary strand oligonucleotide) in Example 1 using TAMRA(5T-NPM1-e12-R2) as a probe.
Figure 10:
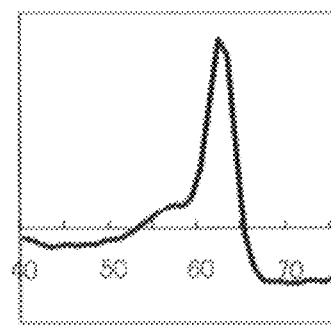
FIG. 10 shows the result of Tm analysis for mt type Q (complementary strand oligonucleotide) in Example 1 using TAMRA(5T-NPM1-e12-R2) as a probe.
Figure 11:
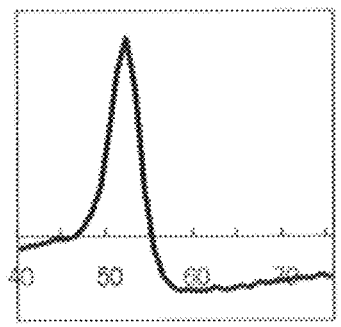
FIG. 11 shows the result of Tm analysis for mt type 10 (complementary strand oligonucleotide) in Example 1 using TAMRA(5T-NPM1-e12-R2) as a probe.
Figure 12:
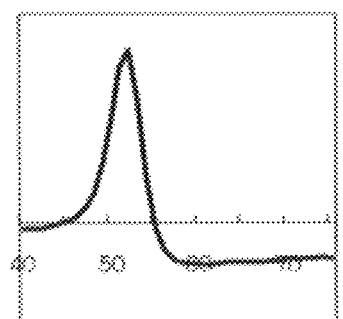
FIG. 12 shows the result of Tm analysis for mt type E (complementary strand oligonucleotide) in Example 1 using TAMRA(5T-NPM1-e12-R2) as a probe.
Figure 13:
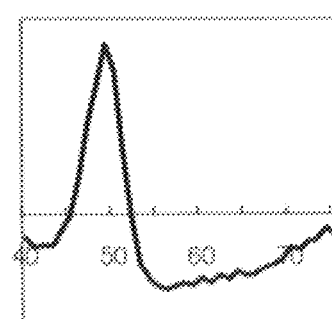
FIG. 13 shows the result of Tm analysis for mt type 6 (complementary strand oligonucleotide) in Example 1 using TAMRA(5T-NPM1-e12-R2) as a probe.
Figure 14:
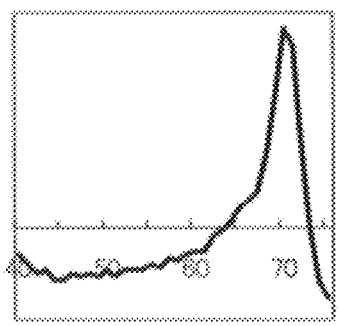
FIG. 14 shows the result of Tm analysis for WT (complementary strand oligonucleotide) in Comparative Example 1 using TAMRA(3T-NPM1-e12-R3) as a probe.
Figure 15:
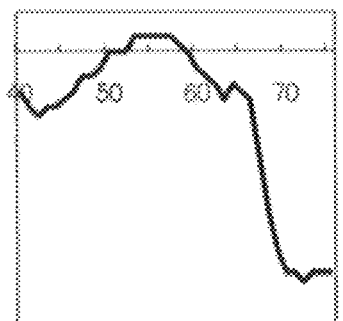
FIG. 15 shows the result of Tm analysis for mt type A (complementary strand oligonucleotide) in Comparative Example 1 using TAMRA(3T-NPM1-e12-R3) as a probe.
Figure 16:
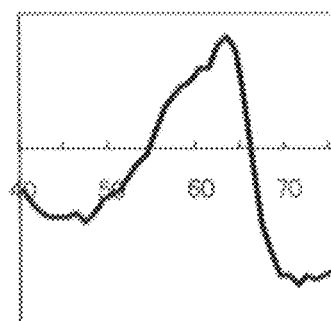
FIG. 16 shows the result of Tm analysis for mt type B (complementary strand oligonucleotide) in Comparative Example 1 using TAMRA(3T-NPM1-e12-R3) as a probe.
Figure 17:
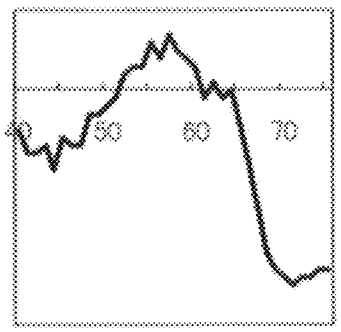
FIG. 17 shows the result of Tm analysis for mt type D (complementary strand oligonucleotide) in Comparative Example 1 using TAMRA(3T-NPM1-e12-R3) as a probe.
Figure 18:
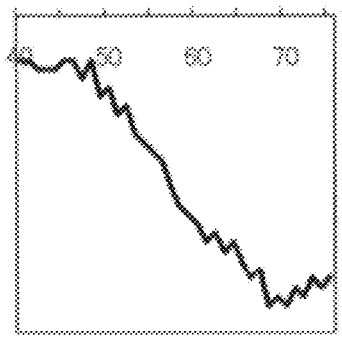
FIG. 18 shows the result of Tm analysis for mt type 7 (complementary strand oligonucleotide) in Comparative Example 1 using TAMRA(3T-NPM1-e12-R3) as a probe.
Figure 19:
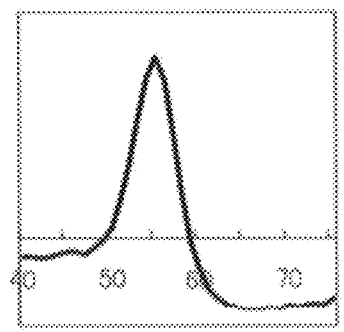
FIG. 19 shows the result of Tm analysis for mt type Q (complementary strand oligonucleotide) in Comparative Example 1 using TAMRA(3T-NPM1-e12-R3) as a probe.
Figure 20:
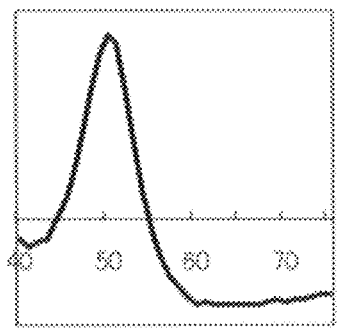
FIG. 20 shows the result of Tm analysis for mt type 10 (complementary strand oligonucleotide) in Comparative Example 1 using TAMRA(3T-NPM1-e12-R3) as a probe.
Figure 21:
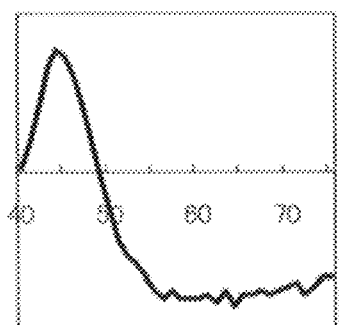
FIG. 21 shows the result of Tm analysis for mt type E (complementary strand oligonucleotide) in Comparative Example 1 using TAMRA(3T-NPM1-e12-R3) as a probe.
Figure 22:
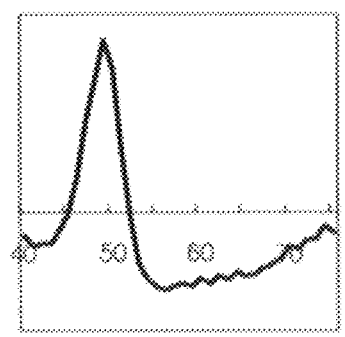
FIG. 22 shows the result of Tm analysis for mt type 6 (complementary strand oligonucleotide) in Comparative Example 1 using TAMRA(3T-NPM1-e12-R3) as a probe.

By using any one of the oligonucleotides (P5), (P5'), (P6), (P6'), (P7), (P7'), (P1), (P1'), (P2) and (P2') described herein; by using three oligonucleotides, for example, (P5), (P6) and (P7), or (P5'), (P6') and (P7'); by using two oligonucleotides, for example, (P1) and (P2), or (P1') and (P2'); by using the probes shown in SEQ ID NOs: 56 to 58 described in Examples 3 and 4 in the present specification; or by using the probes shown in SEQ ID NOs: 4 and 5 described in Examples 1 and 2 in the present specification; a mutation(s) in exon 12 of the NPM1 gene may be be detected (e.g. FIG. 3).

In one aspect, the probe of the present invention emits fluorescence from a fluorescent dye when the probe is not hybridized with the target sequence, and the fluorescence from the fluorescent dye decreases or increases when the probe is hybridized with the target sequence. For example, the probe of the present invention is a quenching probe which emits fluorescence from a fluorescent dye when the probe is not hybridized, and the fluorescence from the fluorescent dye is quenched when the probe is hybridized.

Further, the probe of the present invention according to some embodiments has a base labeled with a fluorescent dye at the first, second or third position from the 5' or 3' end, and the probe according to additional embodiments has the 3' end which is labeled with a fluorescent dye. In the present specification, when the term "first, second or third position from the 5' end" is mentioned, the 5' end is counted as the first position, and, when the term "first, second or third position from the 3' end" is mentioned, the 3' end is counted as the first position.

The nucleotide labeled with a fluorescent dye in the probe of the present invention is the nucleotide at the position corresponding to position 145 in SEQ ID NO:2 in terms of P5, P5', P6, P6', P7 and P7', the nucleotide at the position corresponding to position 135 in SEQ ID NO:1 in terms of P1 and P1', and the nucleotide at the position corresponding to position 182 in SEQ ID NO:1 in terms of P2 and P2'.

The mutations in exon 12 of the NPM1 gene which may be detected by the oligonucleotides of the present invention are, for example, described in Table 1 below, and at least one mutation selected from the group consisting of Type A, Type B, Type D, Type C, Type E, Type Gm, Type Km, Type Nm, Type Om, Type Qm, Type 3, Type 4, Type 6, Type 7, Type 10, Type 13, Type G+, Type H+, Type I+, Type J+, and Type I can be detected.

TABLE 1

Various mutants in exon 12 of the NPM1 gene

| Number of cases of mutation | | | ① | ② | ③④ | ⑤ | ⑥ | ⑦⑧ | ⑨ | ⑩ | ⑪ | SEQ ID NOS |
|---|---|---|---|---|---|---|---|---|---|---|---|---|
| | | Wild-Type | gaccaagaggctattcaagatctct | g | | gcag | | t | | ggagg | aagtctctttaagaaaatag | 18 |
| 494 | x | A | gaccaagaggctattcaagatctct | g | tctg | gcag | | t | | ggagg | aagtctctttaagaaaatag | 19 |
| 49 | x | B | gaccaagaggctattcaagatctct | g | catg | gcag | | t | | ggagg | aagtctctttaagaaaatag | 20 |
| 1 | x | C | gaccaagaggctattcaagatctct | g | cgtg | gcag | | t | | ggagg | aagtctctttaagaaaatag | 21 |
| 49 | x | D | gaccaagaggctattcaagatctct | g | cctg | gcag | | t | | ggagg | aagtctctttaagaaaatag | 22 |

TABLE 1-continued

Various mutants in exon 12 of the NPM1 gene

| Number of cases of mutation | | | ① | ② | ③④ | ⑤ | ⑥ | ⑦⑧ | ⑨ | ⑩ | ⑪ | SEQ ID NOS |
|---|---|---|---|---|---|---|---|---|---|---|---|---|
| 1 | x | E | gaccaagaggctattcaagatctct | | g | | gcag | t | ctcttgccc | | aagtctctttaagaaaatag | 23 |
| 1 | | F | gaccaagaggctattcaagatctct | | g | | gcag | t | ccctggaga | | aagtctctttaagaaaatag | 24 |
| 1 | | E* | gaccaagaggctattcaagatctct | | g | | gcag | t | ccctcgccc | | aagtctctttaagaaaatag | 25 |
| 1 | | G* | gaccaagaggctattcaagatctct | | g | | gcag | t | gcttcgccc | | aagtctctttaagaaaatag | 26 |
| 1 | | H* | gaccaagaggctattcaagatctct | | g | | gcag | t | gtttttcaa | | aagtctctttaagaaaatag | 27 |
| | | J | gaccaagaggctattcaagatctct | | g | | gcag | t ctctttcta | | | aagtctctttaagaaaatag | 28 |
| | | L | gaccaagaggctattcaagatctct cccg | | g | | gcag | t | | | aagtctctttaagaaaatag | 29 |
| | | K | gaccaagaggctattcaagatctct | | g | | gcag | t ccctttcca | | | aagtctctttaagaaaatag | 30 |
| | | M | gaccaagaggctattcaagatctct | | g | tagc | gcag | t | | ggagg | aagtctctttaagaaaatag | 31 |
| | | N | gaccaagaggctattcaagatctct | | | ccac | gcag | t | | ggagg | aagtctctttaagaaaatag | 32 |
| | | O | gaccaagaggctattcaagatctct | | g | | gcag cgtttcc | | | ggagg | aagtctctttaagaaaatag | 33 |
| | | P | gaccaagaggctattcaagatctct | | g | taccttcc | | t | | ggagg | aagtctctttaagaaaatag | 34 |
| 1 | x | Q | gaccaagaggctattcaagatctct | | g | | gcag agga | t | | ggagg | aagtctctttaagaaaatag | 35 |
| 1 | x | Gm | gaccaagaggctattcaagatctct | | g | cagg | gcag | t | | ggagg | aagtctctttaagaaaatag | 36 |
| 3 | x | Km | gaccaagaggctattcaagatctct | | g | ccgg | gcag | t | | ggagg | aagtctctttaagaaaatag | 37 |
| 1 | | Lm | gaccaagaggctattcaagatctct | | g | ccgcgg | ag | t | | ggagg | aagtctctttaagaaaatag | 38 |
| 2 | x | Nm | gaccaagaggctattcaagatctct | | g | ccag | gcag | t | | ggagg | aagtctctttaagaaaatag | 39 |
| 1 | x | Om | gaccaagaggctattcaagatctct | | g | tttg | gcag | t | | ggagg | aagtctctttaagaaaatag | 40 |
| 1 | x | Qm | gaccaagaggctattcaagatctct | | g | tcgg | gcag | t | | ggagg | aagtctctttaagaaaatag | 41 |
| 1 | | 1 | gaccaagaggctattcaagatctct | | g | | gcag tcca | t | | ggagg | aagtctctttaagaaaatag | 42 |
| 1 | x | 3 | gaccaagaggctattcaagatctct | | g | tcat | gcag | t | | ggagg | aagtctctttaagaaaatag | 43 |
| 1 | x | 4 | gaccaagaggctattcaagatctct | | g | cttg | gcag | t | | ggagg | aagtctctttaagaaaatag | 44 |
| 1 | x | 6 | gaccaagaggctattcaagatctct | | g | | gca agatttc ttaaatc | | | | gtctctttaagaaaatag | 45 |
| 1 | x | 7 | gaccaagaggctattcaagatct atgc | ctg | | | gcag | t | | ggagg | aagtctctttaagaaaatag | 46 |
| 1 | | 12 | gaccaagaggctattcaagatctct | | g | gccc | gcag | t | | ggagg | aagtctctttaagaaaatag | 47 |
| 1 | x | 13 | gaccaagaggctattcaagatctct | | g | taag | gcag | t | | ggagg | aagtctctttaagaaaatag | 48 |
| 1 | x | 10 | gaccaagaggctattcaagatctct | | g | | gcag | tg | ctgctccc | | aagtctctttaagaaaatag | 49 |
| 1 | | 14 | gaccaagaggctattcaagatctct | | g | | gcag | t | tattttccc | | aagtctctttaagaaaatag | 50 |
| 1 | x | G+ | gaccaagaggctattcaagatctct | | g | tttg | gcag | t | | ggagg | aagtctctttaagaaaatag | 51 |
| 1 | x | H+ | gaccaagaggctattcaagatctct | | g | cttg | gcag | t | | ggagg | aagtctctttaagaaaatag | 52 |
| 1 | x | I+ | gaccaagaggctattcaagatctct | | g | taag | gcag | t | | ggagg | aagtctctttaagaaaatag | 53 |
| 1 | x | J+ | gaccaagaggctattcaagatctct | | g | tatg | gcag | t | | ggagg | aagtctctttaagaaaatag | 54 |
| | x | I | gaccaagaggctattcaagatctct | | g | caga | gcag | t | | ggagg | aagtctctttaagaaaatag | 55 |

Table 1 shows comparison of sequences of regions in exon 12 among the wild type and various mutant types of the NPM1 gene.
Various mutant sequences have been reported for exon 12 of the NPM1 gene. The numbers of cases reported in several literatures were summarized and described in the left side of the table as "number of cases of mutation". The number of reported cases of the mutant sequence A is considerably large, and the numbers of the reported cases of the mutant sequences B and C are second largest.
In the nucleotide sequences shown in Table 1, for example, the mutant type A has "tctg" inserted at the site 4. Further, the mutant type E has "ctcttgccc" inserted at the site 9 and deletion of "ggagg" at the site 10.
The mutant types whose detection was studied in Examples are marked with "x".

In cases where a probe such as the oligonucleotide (P5), (P5'), (P6), (P6'), (P7) or (P7'), is used, Type A, Type B, Type D, Type C, Type Gm, Type Km, Type Nm, Type Om, Type Qm, Type 3, Type 4, Type 13, Type G+, Type H+, Type I+, Type J+, and Tyepe I and the like may be detected.

In cases where a probe positioned in the 5' side of the region of nucleotides 153 to 156 in the nucleotide sequence shown in SEQ ID NO:1, such as the oligonucleotide (P1) or (P1'), is used, Type A, Type B, Type D, Type 7 and the like may be detected.

In cases where a probe positioned in the 3'side of the region of nucleotides 153 to 156 in the nucleotide sequence shown in SEQ ID NO:1, such as the oligonucleotide (P2) or (P2'), is used, Type 10, Type E, Type 6 and the like may be detected.

Further, by using any one of the oligonucleotides (P5), (P5'), (P6), (P6'), (P7) and (P7') or the oligonucleotides (P1) or (P1') and (P2) or (P2') of the present invention, the presence/absence of the mutations in exon 12 of the NPM1 gene may be detected, and therefore the risk of developing acute myeloid leukemia, and/or the diseased state and/or prognosis of acute myeloid leukemia may be diagnosed.

By using the probes of SEQ ID NOs:56, 57, 58, 4 and 5, as shown in Examples of the present specification, mutations in exon 12 of the NPM1 gene may be detected. The probe shown in SEQ ID NO:56-58, and 4 may be labeled with a dye at its 3' end, and the probe shown in SEQ ID NO:5 may be labeled with a dye at its 5' end. In some embodiments, the dye described herein is a fluorescent dye.

The detection method of the present invention may employ a probe(s) of the present invention as described above. That is, in the detection method according to some embodiments of the present invention, one or more probes each having the region of nucleotides 157 to 160 in the nucleotide sequence shown in SEQ ID NO:2 (corresponding to the region of nucleotides 153 to 156 in the nucleotide sequence shown in SEQ ID NO:1) may be used, or one or more probes selected from the above-described P5, P5', P6, P6', P7 and P7' may be used. Further, one or more probes each having at its end the region of nucleotides 153 to 156 in the nucleotide sequence shown in SEQ ID NO:1 may be used, or one or more probes selected from the above-described P1, P1', P2 and P2' may be used.

For example, the detection method according to additional embodiments of the present invention uses the probe of the present invention and comprises the following:

(I) adding the probe of the present invention to a sample comprising nucleic acid, to allow the probe to hybridize with the nucleic acid;

(II) changing the temperature to dissociate the hybrid-forming body between the nucleic acid and the probe, and measuring fluctuation of a signal due to the dissociation of said hybrid-forming body;

(III) analyzing the fluctuation of a signal to detect the Tm value of single-stranded nucleic acid in the sample; and (IV) determining based on the Tm value the presence or absence of the polymorphism(s) of interest or the abundance ratio(s) of single-stranded nucleic acid having the polymorphism(s) in single-stranded nucleic acid in the sample.

The detection method of the present invention can be carried out in the same manner as conventional methods for nucleic acid amplification and melting curve analysis (Tm analysis) except that the probe described herein is used. Further, the detection method of the present invention may also comprise amplifying nucleic acid before the Step (I) or at the same time with the Step (I).

The method of nucleic acid amplification according to some embodiments uses a polymerase, and examples of the method include PCR, ICAN and LAMP. When the amplification is carried out by a method using a polymerase, the amplification may be carried out in the presence of the probe of the present invention. Those skilled in the art can easily control reaction conditions and the like of the amplification depending on the probe to be used. By this, the detection can be carried out just by analyzing the Tm value of the probe after the amplification of nucleic acid, so that the amplification product does not need to be handled after the reaction. Therefore, there is no risk of contamination by an amplification product. Further, since the detection can be carried out with the same apparatus as the one necessary for the amplification, it is not necessary even to transfer the container. Therefore, automation can also be easily done.

The determination of the Tm value in Step (III) includes not only determination of the temperature of Tm but also determination of the height of the peak at Tm. With the height of the peak, the abundance ratio of a nucleotide sequence having a polymorphism can be determined. For more quantitative determination of the abundance ratio of a nucleotide sequence having a polymorphism, a calibration curve may be prepared as described herein, and the abundance ratio based on the prepared calibration curve may be determined The method of quantitative determination of the abundance ratios of nucleotide sequences having a polymorphism is shown below by way of an example of determination of the abundance ratios of the wild type and a particular variant. However, this is merely an example, and the method of determination of the abundance ratios of nucleotide sequences having a polymorphism is not restricted thereto.

First, a plurality of nucleic acid mixtures in which two types of nucleic acids, that is, the wild-type nucleic acid (Wt) and a variant nucleic acid (Mt), are contained at various abundance ratios are prepared, and a melting curve is obtained for each of the plurality of nucleic acid mixtures using a melting curve analysis device or the like.

FIG. 1(A) shows a melting curve represented as the relationship between the temperature and the fluorescence intensity for a certain nucleic acid mixture, and FIG. 1(B) shows a melting curve represented as the relationship between the temperature and the differential value of the fluorescence intensity (also referred to as a differential melting curve). By detecting a peak from this differential melting curve, $Tm_W$, which is the melting temperature of the nucleic acid Wt, and $Tm_M$, which is the melting temperature of the nucleic acid Mt, are detected, and each of the temperature ranges including $Tm_W$ and $Tm_M$ are set. For example, as $\Delta T_w$, which is the temperature range including $Tm_W$, the temperature range whose lower limit is the temperature at which the differential value of the fluorescence intensity is minimum between $Tm_W$ and $Tm_M$ and whose upper limit is the temperature corresponding to the skirt of the peak of the fluorescence intensity can be set. Further, for example, as $\Delta T_M$, which is the temperature range including $Tm_M$, the temperature range whose upper limit is the temperature at which the differential value of the fluorescence intensity is minimum between $Tm_W$ and $Tm_M$ and whose lower limit is the temperature corresponding to the skirt of the peak of the fluorescence intensity can be set. The temperature range $\Delta T_w$ and the temperature range $\Delta T_M$ may be set such that these have either the same width (e.g., 10° C.) or different widths (e.g., a temperature range $\Delta T_w$ of 10° C. and a temperature range $\Delta T_M$ of 7° C.). Further, the temperature range $\Delta T_w$ and the temperature range $\Delta T_M$ may be set such that each of these has a width ranging from X° C. higher than the melting temperature to X° C. lower than the melting temperature (e.g., X° C. may not be more than 15° C. or, in some instrances, 10° C.).

Subsequently, for each of the temperature range $\Delta T_w$ and the temperature range $\Delta T_M$, the area surrounded by the line passing through the point corresponding to the lower limit and the point corresponding to the upper limit of the temperature range of the differential melting curve, and the differential melting curve (shaded portion in FIG. 1(B)) is calculated. More particularly, for example, the area can be calculated as follows. By defining the differential value of the fluorescence intensity at temperature T as f(T) and the base value at temperature T as B(T), the area is calculated by the Equation (1) below.

$$\text{Area } S = \{f(T_{s+1}) - B(T_{s+1})\} + \{f(T_{s+2}) - B(T_{s+2})\} + \ldots + \{f(T_{e-1}) - B(T_{e-1})\} \quad (1)$$

In the equation, $T_s$ represents the lower limit value of each temperature range, and $T_e$ represents the upper limit value. The base value B(T) at each temperature T is a value calculated by the Equation (2) below and represents the background level contained in the detection signal of the fluorescence intensity. By subtracting this base value from the differential value of the fluorescence intensity, the effect of the background contained in the detection signal of the fluorescence intensity is removed.

$$B(T) = a \times (T - T_s) + f(T_s) \quad (2)$$

In this equation, $a = \{f(T_c) - f(T_s)\}/(T_c - T_s)$.

According to the above Equation (1) and Equation (2), the area $S_w$ in the temperature range $\Delta T_W$ and the area $S_M$ in the temperature range $\Delta T_W$ are calculated, to prepare a calibration curve representing the relationship between the area ratio and the abundance ratio of the respective mixtures. FIG. 2 shows an example of the calibration curve prepared by plotting the abundance ratio (the ratio of nucleic acid Mt with respect to the total amount of the nucleic acid mixture) along the abscissa and the area ratio ($S_M/S_W$) along the ordinate. The area ratio may also be defined as $S_W/S_M$.

By calculating the area ratio from the melting curve and the differential melting curve obtained using an actual sample and preliminarily preparing a calibration curve as described above, the abundance ratio of a nucleotide sequences having a polymorphism contained in the actual sample may be determined based on the prepared calibration curve.

In the present invention, the DNA in the sample may be either single-stranded DNA or double-stranded DNA. In cases where the DNA is double-stranded DNA, for example, the step of dissociating the double-stranded DNA in the sample by heating may be included before the hybridization step. By dissociating the double-stranded DNA into single-stranded DNA, hybridization with a detection probe is possible in the subsequent hybridization step.

In the present invention, the ratio (molar ratio) of the probe of the present invention to be added with respect to the DNA in the sample is not restricted, and the ratio may be 1 or less, 0.5 or less, 0.1 or less with respect to the DNA in the sample in view of securing a sufficient detection signal. In this case, for example, the DNA in the sample may be either the total of the DNA having the polymorphism to be detected and DNA which does not have the polymorphism to be detected, or the total of the amplification product containing the sequence having the polymorphism to be detected and amplification products containing sequences which do not have the polymorphism to be detected. Although the ratio of the DNA to be detected in the DNA in the sample is usually not known, the ratio (molar ratio) of the probe to be added with respect to the DNA to be detected (the amplification product containing the sequence to be detected) is, for example, 10 or less, 5 or less, or 3 or less as a result. The lower limit of the ratio is not restricted, and the ratio is, for example, 0.001 or more, 0.01 or more, 0.1 or more.

The ratio of the probe of the present invention to be added with respect to the DNA may be, for example, either the molar ratio with respect to the double-stranded DNA or the molar ratio with respect to the single-stranded DNA.

Determination of the Tm value will now be described. Heating a solution containing double-stranded DNA causes increase in the absorbance at 260 nm. This is caused because hydrogen bonds between the both strands of the double-stranded DNA are unraveled by the heat and the double-stranded DNA is dissociated into single-stranded DNA (melting of DNA). Based on this phenomenon, the melting temperature Tm can be generally defined as the temperature at which increase in the absorbance reached 50% of the total increase in the absorbance.

In the present invention, the difference in the Tm value when the above-mentioned labeled oligonucleotides P5, P5', P6, P6', P7, P7', P1, P1', P2, and P2' hybridized with a nucleotide which is complementary thereto and when the above-mentioned labeled oligonucleotides P5, P5', P6, P6', P7, P7', P1, P1', P2, and P2' hybridized with a nucleotide which is not complementary thereto, is more than 5° C., for example. When the difference in the Tm value is 5° C. or more, the above-mentioned mutants can be detected with high sensitivity.

As for the difference in the Tm value, 5° C. or more, 7° C. or more is exemplified.

As for a method for increasing the difference in the Tm value, a method wherein a probe is designed to include nucleotides mismatched to a nucleotide sequence to be hybridized, or a method described in Nature Biotech (1997) vol. 15, p. 331-335 is exemplified.

In the present invention, measurement of the signal fluctuation due to the temperature change for determination of the Tm value can be carried out also by measuring the absorbance at 260 nm based on the above-mentioned principle, but the measurement may be carried out based on a signal from a label added to the probe of the present invention, which signal fluctuates depending on the state of hybrid formation between the DNA and the probe. Therefore, as the probe of the present invention, the above-mentioned labeled probe may be used. Examples of the labeled probe include a fluorescently labeled oligonucleotide probe which emits fluorescence when it is not hybridized with the target sequence, whose fluorescence intensity decreases (the fluorescence is quenched) when the probe is hybridized with the target sequence, and a fluorescently labeled oligonucleotide probe which emits fluorescence when it is not hybridized with the target sequence, whose fluorescence intensity increases when the probe is hybridized with the target sequence. In the case of the former probe, the probe shows no signal or a weak signal when it is forming a hybrid (double-stranded DNA) with the sequence to be detected, while the probe shows a signal or the signal increases when the probe is released by heating. In the case of the latter probe, the probe shows a signal by forming a hybrid (double-stranded DNA) with the sequence to be detected, while the signal decreases (disappears) when the probe is released by heating. Therefore, by detecting the change in the signal due to the label under conditions specific to the signal (absorbance and the like), determination of the progress of melting and the Tm value can be carried out similarly to the case of the measurement of the absorbance at 260 nm. For example, the labeling substance in the labeled probe is as mentioned above, and the probe may be labeled with a fluorescent dye.

The nucleic acid to be used as a template for carrying out the nucleic acid amplification is not restricted as long as it contains nucleic acid, and examples of the nucleic acid include those derived from, or those which may be derived from, arbitrary biological origins such as blood; oral mucosal suspensions; somatic cells of nails, hairs and the like; germ cells; milks; ascitic fluids; paraffin-embedded tissues; gastric juices; fluids obtained by gastric lavage; peritoneal fluids; amniotic fluids; and cell cultures. The nucleic acid as a template may be used as it is directly after being obtained from the origin, or may be pretreated to modify properties of the sample before being used.

The method of nucleic acid amplification is further described by way of an example using PCR. The primer pair used in the PCR may be designed in the same manner as in the method for designing a primer pair for conventional PCR, except that the primer pair is designed such that a region with which the probe of the present invention can hybridize is amplified. The length and the Tm value of each primer is usually 12 mer to 40 mer and 40 to 70° C., or 16 mer to 30 mer and 55 to 60° C., respectively. The length of the respective primers of the primer pair does not need to be the same, but the Tm values of the both primers may be almost the same (the difference is usually not more than 2° C.). The Tm value is a value calculated by the Nearest Neighbor method. Examples of the primer pair include the one composed of the primers having the nucleotide sequences shown in SEQ ID NOs:16 and 17.

The PCR may be carried out in the presence of the probe described herein. By this, the Tm analysis may be carried out without subjecting the amplified product to purification and/or the like after the amplification reaction. Those skilled in the art can easily control the Tm values of the primers and the reaction conditions for the PCR depending on the probe used.

The detection of a mutation(s) in exon 12 of the NPM1 gene based on the result of Tm analysis can be carried out according to a conventional method. The detection herein includes detection of the presence/absence of a mutation(s) and determination of the abundance ratio(s) of a nucleic acid(s) having a polymorphism(s).

By using the probe and the method for detecting a polymorphism(s) of the present invention, a mutation(s) in exon 12 of the NPM1 gene can be detected, and the risk of developing acute myeloid leukemia, and/or the diseased state and/or prognosis of acute myeloid leukemia can be diagnosed based on the detected presence/absence of the mutation(s).

<2> Kit of Present Invention

The kit according to some embodiments of the present invention is a kit which employs the detection method of the present invention. This kit may comprise the probe of the present invention for detecting a polymorphism(s). The kit may also determine the risk of developing acute myeloid leukemia, and/or the diseased state and/or prognosis of acute myeloid leukemia. The probe is as described herein as the probe of the present invention.

The detection kit of the present invention may further comprise, in addition to the probe, reagents required for nucleic acid amplification in the detection method of the present invention, especially the above-described primers for amplification using a DNA polymerase.

In the detection kit of the present invention, the probe, primers and other reagents may be contained separately, or a mixture of a part of them may be contained in the kit.

In the present invention, in terms of the individual sequences in the sample nucleic acids, probes for detecting a polymorphism(s) and primers, matters described based on the complementary relationship between these are applied to the respective sequences and also to the sequences complementary thereto unless otherwise specified. When the matters of the present invention are applied to the sequence complementary to each sequence, the sequence recognized by the complementary sequence is read as the sequence complementary to the corresponding sequence described in the present specification throughout the specification according to the common technical knowledge.

The present invention will now be described further by way of Examples. However, these Examples are merely examples, and the present invention is not restricted to the Examples.

EXAMPLES

Example 1

Detection from Complementary Strand Oligonucleotide Using Probes P1 and P2

Based on the nucleotide sequence of exon 12 of the NPM1 gene (SEQ ID NO:1 (wild type)), the probes having C at their ends shown in table 2 were designed. In table 2, the position of each probe is indicated by its nucleotides in the nucleotide sequence shown in SEQ ID NO:1. "P" at the 3' end indicates phosphorylation. Labeling with TAMRA was carried out according to a conventional method.

The sequences of the complementary strand oligonucleotides used as the subjects of detection are shown in Table 2. In Table 2, the position of each oligonucleotide is indicated by its nucleotides in the nucleotide sequence shown in SEQ ID NO:1. In Table 2, bases represented by uppercase letters indicate the position of mutation which is characteristic to each mutation.

TABLE 2

| SEQ ID NO: | Probe name | Sequence (5'→3') | Positions | Mer |
|---|---|---|---|---|
| 4 | 3T-NPM1-e12-R1 | tgccagagatcttgaatagcc-(TAMRA) | 155-135 | 21 |
| 5 | 5T-NPM1-e12-R2 | (TAMRA)-ctattttcttaaagagacttcctccac-P | 182-156 | 27 |

| SEQ ID NO: | Name of complementary strand oligonucleotide | Sequence (5'→3') | Positions | mer |
|---|---|---|---|---|
| 6 | WT | ccaggctattcaagatctctggcagtggaggaagtctctttaagaaaatagttt | 132-185 | 54 |
| 7 | mt type A | ccaggctattcaagatctctgTCTGgcagtggaggaagtctctttaagaaaatagttt | | 58 |
| 8 | mt type B | ccaggctattcaagatctctgCATGgcagtggaggaagtctctttaagaaaatagttt | | 58 |
| 9 | mt type D | ccaggctattcaagatctctgCCTGgcagtggaggaagtctctttaagaaaatagttt | | 58 |
| 10 | mt type 7 | ccaggctattcaagatctATGCctggcagtggaggaagtctctttaagaaaatagttt | | 58 |
| 11 | mt type Q | ccaggctattcaagatctctggcagAGGAtggaggaagtctctttaagaaaatagttt | | 58 |
| 12 | mt type 10 | ccaggctattcaagatctctggcagtgCTGCTCCCaagtctctttaagaaaatagttt | | 58 |
| 13 | mt type E | ccaggctattcaagatctctggcagtCTCTTGCCCaagtctctttaagaaaatagttt | | 58 |
| 14 | mt type 6 | ccaggctattcaagatctctggcaAGATTTCTTAAATCgtctctttaagaaaatagttt | | 59 |

In order to confirm the performances of probes designed for detecting mutations in the exon 12 region of the NPM1 gene with 2 probes, the complementary strands of the wild-type sequence and various mutant sequences of the NPM1 exon 12 region were prepared, and the following reagent solution comprising a probe and a complementary strand oligonucleotide was prepared.

To the probe 3T-NPM1-e12-R1, WT or mt type A, B, D, or 7 was added as the complementary strand oligonucleotide, and, to the probe 5T-NPM1-e12-R2, WT or mt type Q, 10, E, or 6 was added as the complementary strand oligonucleotide.

TABLE 3

| Formulation: total amount, 25 µl | |
|---|---|
| 1x GeneTaq Buffer | |
| Probe * | 0.2 µM |
| Template oligonucleotide (WT, mt) | 0.5 µM |

The conditions of the Tm analysis were as follows. The excitation wavelength and the detection wavelength in the Tm analysis were 520 to 555 nm and 585 to 700 nm (TAMRA), respectively.

The prepared reagent solution was added to an i-densy reaction tube, and 30 µL of mineral oil was overlaid on the solution to prevent evaporation of the reagent. Tm analysis was carried out under the following reaction conditions to analyze the amount of change in the fluorescence value of TAMRA.

TABLE 4

Conditions for Tm analysis

95° C., 1 sec.
↓
40° C., 60 sec.
↓
40° C. ⟶ 80° C., 1° C./3 sec.

As a result of the Tm analysis using the probes shown in Table 2, peaks of TAMRA were observed with 3T-NPM1-e12-R1 (SEQ ID NO:4) at about 65° C. (WT), 59° C. (Type A), 60° C. (Type B), 60° C. (Type D) and 55° C. (Type 7) (FIGS. 4 to 8).

Thus, a detection peak was observed for WT and each of the mutations. Further, it was proved that the difference in the Tm value (ΔTm) between WT and each mutation was 5 to 10° C., which is sufficient for detecting the mutation. Thus, the probe was proved to be suitable for detecting the mutations.

The results are shown in Table 5.

TABLE 5

| | Tm (° C.) | ΔTm (° C.) |
|---|---|---|
| WT | 65 | — |
| A | 59 | 6 |
| B | 60 | 5 |
| D | 60 | 5 |
| 7 | 55 | 10 |

Further, peaks of TAMRA were observed with 5T-NPM1-e12-R2 (SEQ ID NO:5) at about 64° C. (WT), 62° C. (Type Q), 52° C. (Type 10), 52° C. (Type E) and 49° C. (Type 6) (FIGS. 9 to 13).

Thus, a detection peak was observed for WT and each of the mutations. Further, it was proved that, although the difference in the Tm value (ΔTm) between WT and the Type Q mutation was 2° C., the other mutant types showed sufficient difference in the Tm value, suggesting that the probe is suitable for detecting the mutations.

The results are shown in Table 6.

TABLE 6

| | Tm (° C.) | ΔTm (° C.) |
|---|---|---|
| WT | 64 | — |
| Q | 62 | 2 |
| 10 | 52 | 12 |
| E | 52 | 12 |
| 6 | 49 | 15 |

Based on the results of Example 1, when the probes P1 (SEQ ID NO:4) and P2 (SEQ ID NO:5) were used, changes in the fluorescence intensity which can be analyzed by Tm analysis was observed for the polymorphisms of mutations (Type A, Type, B, Type D, Type 7, Type 10, Type E and Type 6) in exon 12 of the NPM1 gene. That is, each of the mutant types has another peak in addition to the peak for the wild type, and a unique pattern of the amount of change in the fluorescence intensity exists. Therefore, by using the probes P1 (SEQ ID NO:4) and P2 (SEQ ID NO:5), the polymorphisms of mutations in exon 12 of the NPM1 gene can be detected.

Comparative Example 1

Detection from Complementary Strand Oligonucleotide

In order to confirm the performance of a probe designed for detecting mutations in the exon 12 region of the NPM1 gene with a single probe, the complementary strands of the wild-type sequence and various mutant sequences of the NPM1 exon 12 region were prepared, and the following reagent solution comprising the probe and each complementary strand oligonucleotide was prepared.

The reagent solution was the same as in Example 1 except that the probe described below was used. Tm analysis was also carried out in the same manner as in Example 1.

The sequence of the probe used for detection of the mutations is shown in Table 7. In Table 7, the position of the probe is indicated as nucleotides in the nucleotide sequence shown in SEQ ID NO:1.

TABLE 7

| SEQ ID NO: | Probe name | Sequence (5'→3') | Positions | mer |
|---|---|---|---|---|
| 15 | 3T-NPM1-e12-R3 | gagacttcctccactgccagagatc-(TAMRA) | 169-145 | 25 |

Although the detection was achieved without any problem for WT and some of the mutant types, no detection peak was found for the mutant types A, D and 7, and it was therefore proved that the probe is not suitable for detection of various mutations (FIGS. 14 to 22). The results are shown in Table 8.

TABLE 8

|    | Tm (° C.)    | ΔTm (° C.) |
|----|--------------|------------|
| WT | 70           | —          |
| A  | Undetectable |            |
| B  | 63           | 7          |
| D  | Undetectable |            |
| 7  | Undetectable |            |
| Q  | 63           | 7          |
| 10 | 55           | 15         |
| E  | 50           | 20         |
| 6  | 44           | 26         |

Example 2

Detection from Blood Sample or Artificial Nucleic Acid Plasmid

In order to study whether detection by Tm analysis is possible after nucleic amplification, the reaction was performed using a blood sample. Further, in order to study how much proportion a mutation in exon 12 of the NPM1 gene should be contained in a sample to allow detection of the mutation, detection waveforms obtained with various mixing ratios between artificial nucleic acid plasmids of the wild-type sequence and a mutant sequence (Type A or Type E) were observed. As the artificial nucleic acids, plasmids were prepared by insertion of the wild-type sequence around exon 12 of the NPM1 gene (590 bp, SEQ ID NO:1), the mutant type A (594 bp, SEQ ID NO:2) or the mutant type E (594 bp, SEQ ID NO:3) to pUC plasmid vector.

The PCR and Tm analysis were carried out using a fully automatic SNPs testing device (trade name: i-densy IS-5310, manufactured by ARKRAY, Inc.). The conditions of the PCR and Tm analysis were as shown in Table 11 below.

The sequences of the probes and the primers used for detection of mutations are shown in Table 12. In Table 12, the positions of the probes and the primers are indicated as nucleotides in the nucleotide sequence shown in SEQ ID NO:1.

The excitation wavelength and the detection wavelength in the Tm analysis were 420 to 485 nm and 520 to 555 nm, respectively (BODIPY FL), or 520 to 555 nm and 585 to 700 nm, respectively (TAMRA).

The reagent solution was as follows.

TABLE 9

| (Reaction solution volume: 50 μl) | |
|---|---|
| 1x PCR buffer | |
| dNTP | 0.2 mM |
| MgCl$_2$ | 1.5 mM |
| Taq polymerase (manufactured by ARKRAY, Inc.) | 1.88 U/test |

TABLE 9-continued

| (Reaction solution volume: 50 μl) | |
|---|---|
| 1x PCR buffer | |
| NPM1-F2 | 1 μM |
| NPM1-R4 | 0.5 μM |
| 3FL-NPM1-e12-R1 | 0.8 μM |
| 5T-NPM1-e12-R2 | 0.8 μM |
| template | 4 μl |

<Preparation of Whole Blood>

To 70 μl of a diluent (1), 10 μl of whole blood was added, and the resulting mixture was mixed well, followed by adding 10 μl of the resulting mixture to 70 μl of a diluent (2). A 17-μl aliquot of the mixture was then heated at 95° C. for 10 minutes, to obtain 4 μl of pretreated whole blood. This was used as a template for each test.

TABLE 10

| Diluent (1) | |
|---|---|
| Tris-HCl (pH8.0) | 10 mM |
| EDTA (pH8.0) | 0.1 mM |
| SDS | 0.30% |
| Diluent (2) | |
| Tris-HCl (pH8.0) | 10 mM |
| 500 mM EDTA (pH8.0) | 0.1 mM |

<Artificial Nucleic Acid Plasmid>

The wild type and a mutant type were mixed to prepare an artificial nucleic acid plasmid at a concentration of 500 copies/μl, and 4 μl of the resulting artificial nucleic acid plasmid was used.

TABLE 11

Conditions for PCR and Tm analysis

95° C., 60 sec.

↓

(95° C., 1 sec., 58° C., 15 sec.) × 50

↓

95° C., 1 sec.

↓

40° C., 60 sec.

↓

40° C. ⟶ 75° C., 1° C./3 sec.

TABLE 12

| SEQ ID NO:Name | sequence (5'→3') | Positions | mer |
|---|---|---|---|
| 4 | 3FL-NPM1-e12-R1 | tgccagagatcttgaatagcc-(BODIPY FL) | 155-135 | 21 |

TABLE 12-continued

| SEQ ID NO: | Name | sequence (5'→3') | Positions | mer |
|---|---|---|---|---|
| 5 | 5T-NPM1-e12-R2 | (TAMRA)-ctattttcttaaagagacttcctccac-P | 182-156 | 27 |
| 16 | NPM1-F2 | gatgtctatgaagtgttgtggttcct | 81-116 | 26 |
| 17 | NPM1-R4 | caactgttacagaaatgaaataagacggaaa | 235-205 | 31 |

Figure 23:
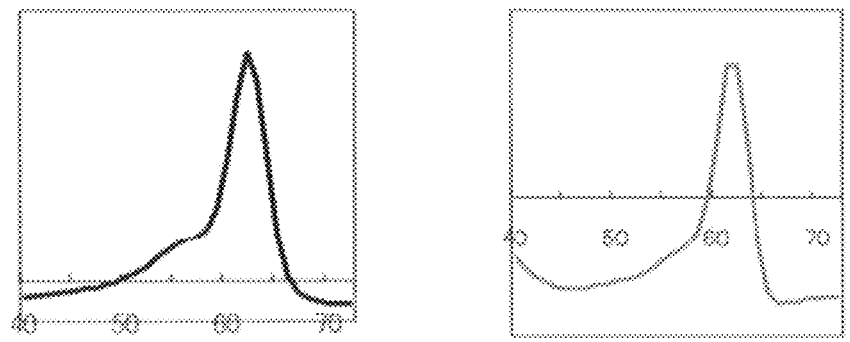
FIG. 23 shows the results of Tm analysis after PCR reaction for the blood sample in Example 2 using BODIPY FL(3FL-NPM1-e12-R1) (left) and TAMRA(5T-NPM1-e12-R2) (right) as probes.

As a result of measurement with the blood sample using i-densy, a detection peak was observed without any problem (FIG. 23).

Figure 24:
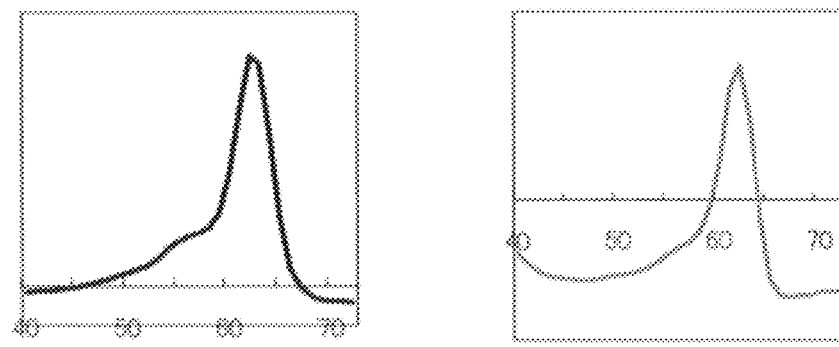
FIG. 24 shows the results of Tm analysis after PCR reaction for WT 100% (plasmid) in Example 2 using BODIPY FL(3FL-NPM1-e12-R1) (left) and TAMRA(5T-NPM1-e12-R2) (right) as probes.

The detection waveform obtained using the artificial nucleic acid plasmid was observed, and, as a result, the detection peak of the wild type was found at 63° C. in the case of BODIPY FL and similarly at 63° C. in the case of TAMRA (FIG. 24).

Figure 25:
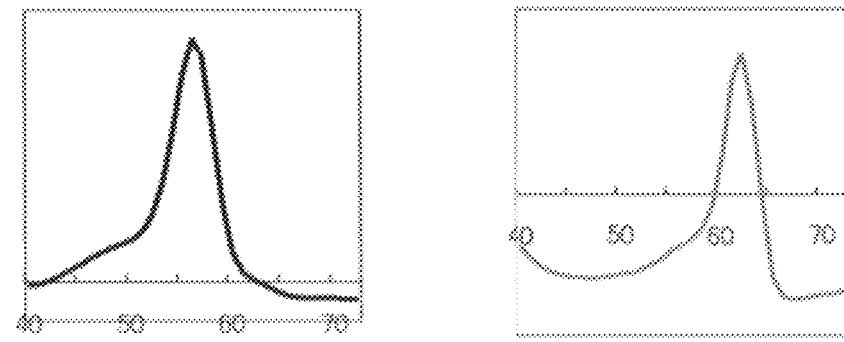
FIG. 25 shows the results of Tm analysis after PCR reaction for mt type A 100% (plasmid) in Example 2 using BODIPY FL(3FL-NPM1-e12-R1) (left) and TAMRA(5T-NPM1-e12-R2) (right) as probes.
Figure 26:
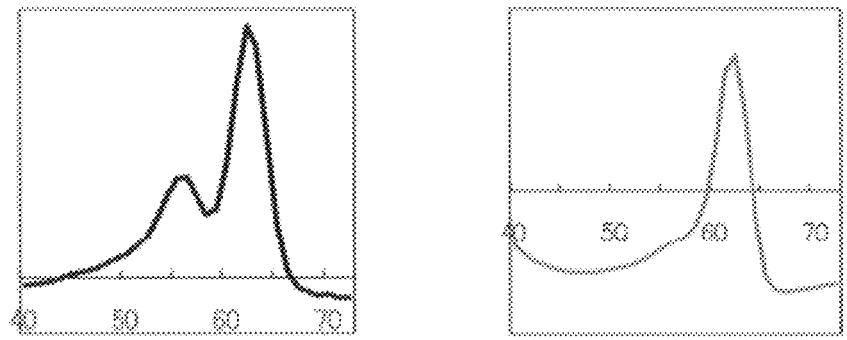
FIG. 26 shows the results of Tm analysis after PCR reaction for mt type A 30% and Wt 70% (plasmids) in Example 2 using BODIPY FL(3FL-NPM1-e12-R1) (left) and TAMRA(5T-NPM1-e12-R2) (right) as probes.
Figure 27:
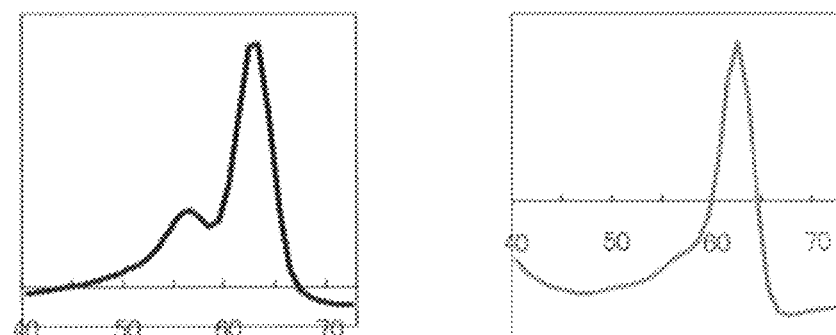
FIG. 27 shows the results of Tm analysis after PCR reaction for mt type A 20% and Wt 80% (plasmids) in Example 2 using BODIPY FL(3FL-NPM1-e12-R1) (left) and TAMRA(5T-NPM1-e12-R2) (right) as probes.
Figure 28:
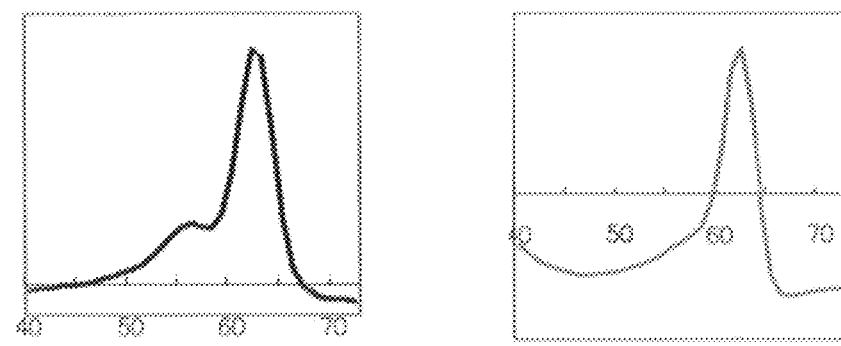
FIG. 28 shows the results of Tm analysis after PCR reaction for mt type A 10% and Wt 90% (plasmids) in Example 2 using BODIPY FL(3FL-NPM1-e12-R1) (left) and TAMRA(5T-NPM1-e12-R2) (right) as probes.
Figure 29:
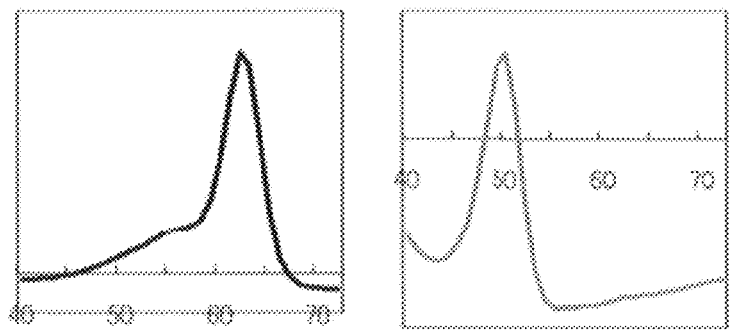
FIG. 29 shows the results of Tm analysis after PCR reaction for mt type E 100% (plasmid) in Example 2 using BODIPY FL(3FL-NPM1-e12-R1) (left) and TAMRA(5T-NPM1-e12-R2) (right) as probes.
Figure 30:
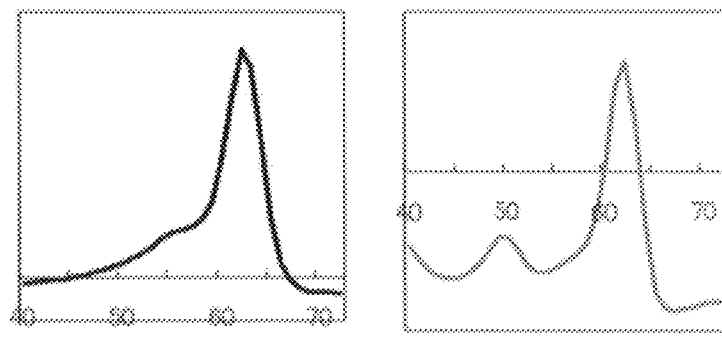
FIG. 30 shows the results of Tm analysis after PCR reaction for mt type E 30% and Wt 70% (plasmids) in Example 2 using BODIPY FL(3FL-NPM1-e12-R1) (left) and TAMRA(5T-NPM1-e12-R2) (right) as probes.
Figure 31:
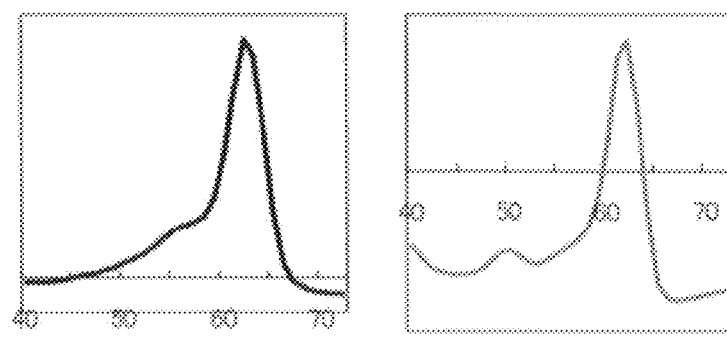
FIG. 31 shows the results of Tm analysis after PCR reaction for mt type E 20% and Wt 80% (plasmids) in Example 2 using BODIPY FL(3FL-NPM1-e12-R1) (left) and TAMRA(5T-NPM1-e12-R2) (right) as probes.
Figure 32:
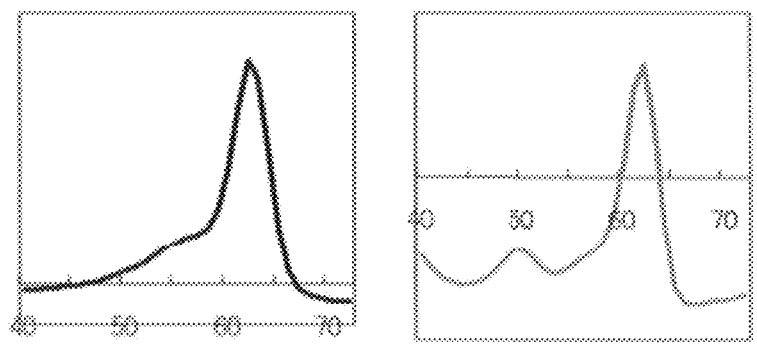
FIG. 32 shows the results of Tm analysis after PCR reaction for mt type E 10% and Wt 90% (plasmids) in Example 2 using BODIPY FL(3FL-NPM1-e12-R1) (left) and TAMRA(5T-NPM1-e12-R2) (right) as probes.

In the case of the mutant type A, a detection peak with BODIPY FL was found at 56 to 57° C. (FIG. 25, left), and in the case of the mutant type E, a detection peak with TAMRA was found at 50 to 51° C. (FIG. 29, right). In the cases of a plasmid with an arbitrary mixing ratio, a detection peak of either the mutant type A or E was found even in the state wherein the mutant sequence is mixed at a ratio of 10% (FIG. 28, left; FIG. 32, right).

Based on the results of Example 2, when the probes P1 (SEQ ID NO:4) and P2 (SEQ ID NO:5) were used, when a blood sample was used, and even when a mutant sequence was mixed at a ratio of 10%, changes in the fluorescence intensity which can be analyzed by Tm analysis was observed for the polymorphisms of mutations (Type A and Type E) in exon 12 of the NPM1 gene. Therefore, by using the probes P1 (SEQ ID NO:4) and P2 (SEQ ID NO:5), the polymorphisms of mutations in exon 12 of the NPM1 gene can be detected.

Comparative Example 2

As a comparative example, the 3T-NPM1-e12-R3 probe was used. Whether detection by Tm analysis is possible after nucleic acid amplification using the following solution was studied. The primer sequences and the reaction conditions were the same as in Example 2. In a reaction tube, 4 µL of a plasmid solution (500 copies/µL) was added, and the reaction was carried out under the following reaction conditions using i-densy. In Tm analysis, the amount of change in the fluorescence value of TAMRA was analyzed.

TABLE 13

| (Reaction solution volume: 50 µl | |
|---|---|
| 1 × PCR buffer | |
| dNTP | 0.2 mM |
| MgCl₂ | 1.5 mM |
| Taq polymerase (manufactured by ARKRAY, Inc.) | 1.88 U/test |
| NPM1-F2 | 1 µM |
| NPM1-R4 | 0.5 µM |
| 5T-NPM1-e12-R3 | 0.8 µM |
| template | 4 ml |

| SEQ ID NO: | Probe name | Sequence (5'→3') | mer |
|---|---|---|---|
| 15 | 3T-NPM1-e12-R3 | gagacttcctccactgccagagatc-(TAMRA) | 25 |

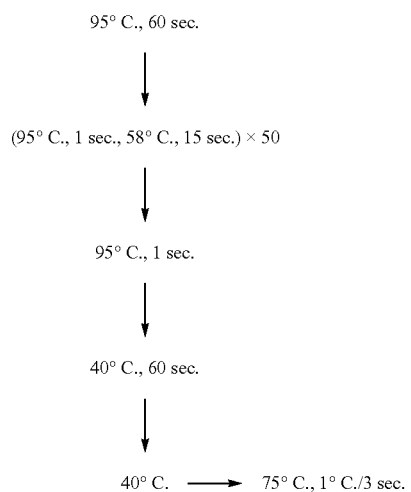

TABLE 14

Conditions for PCR and Tm analysis

95° C., 60 sec.
↓
(95° C., 1 sec., 58° C., 15 sec.) × 50
↓
95° C., 1 sec.
↓
40° C., 60 sec.
↓
40° C. → 75° C., 1° C./3 sec.

Figure 33:
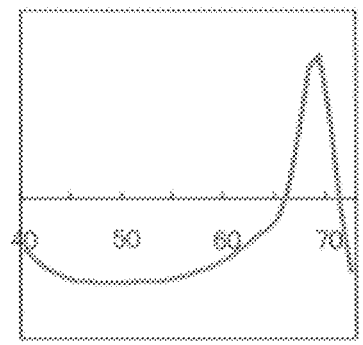
FIG. 33 shows the result of Tm analysis after PCR reaction for the blood sample in Comparative Example 2 using TAMRA(3T-NPM1-e12-R3) as a probe.
Figure 34:
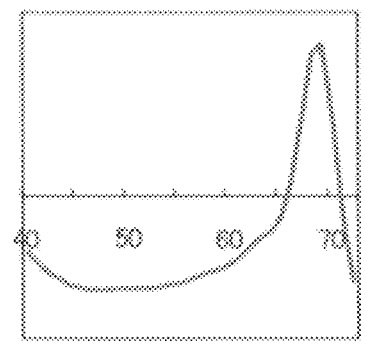
FIG. 34 shows the result of Tm analysis after PCR reaction for WT 100% (plasmid) in Comparative Example 2 using TAMRA(3T-NPM1-e12-R3) as a probe.
Figure 35:
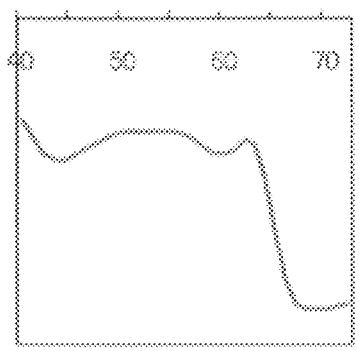
FIG. 35 shows the result of Tm analysis after PCR reaction for mt type A 100% (plasmid) in Comparative Example 2 using TAMRA(3T-NPM1-e12-R3) as a probe.
Figure 36:
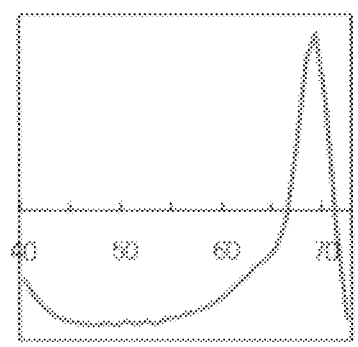
FIG. 36 shows the result of Tm analysis after PCR reaction for mt type A 20% and WT 80% (plasmids) in Comparative Example 2 using TAMRA(3T-NPM1-e12-R3) as a probe.
Figure 37:
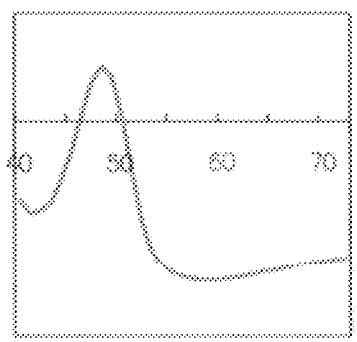
FIG. 37 shows the result of Tm analysis after PCR reaction for mt type E 100% (plasmid) in Comparative Example 2 using TAMRA(3T-NPM1-e12-R3) as a probe.
Figure 38:
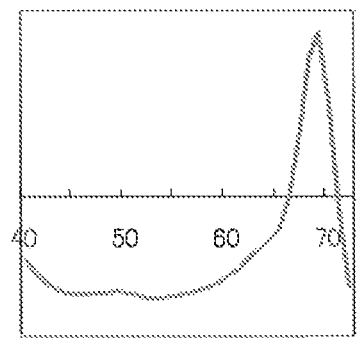
FIG. 38 shows the result of Tm analysis after PCR reaction for mt type E 20% and Wt 80% (plasmids) in Comparative Example 2 using TAMRA(3T-NPM1-e12-R3) as a probe.

In the case where blood was used and in the cases where the wild type and the mutant type E as artificial nucleic acid plasmids were used, detection peaks were obtained without any problem (FIGS. 33, 34 and 37). However, the detection peak could not be found in the case where the mutant type A 100% was used as a sample (FIG. 35). Further, in the cases where an artificial nucleic acid in which the mutant type A or E was mixed at a ratio of 20% was used, the detection peak for the mutant type was not observed, and only the detection peak for the wild type was observed (FIGS. 36 and 38). From these results, it is judged that, in contrast to the results in Example 2, the 3T-NPM1-e12-R3 probe is unsuitable for detection of mutations in exon 12 of NPM1.

Example 3

Detection from Complementary Strand Oligonucleotide using Probes P5, P6 and P7

As for exon 12 of the NPM1 gene, many mutated sequences are reported and most of them are Type A, Type B or Type D (See Table 1). Thus, the important factor of a probe for detecting exon 12 mutations in the NPM1 gene is the ability to detect Type A, Type B and Type D clearly.

Based on the nucleotide sequence of exon 12 of the NPM1 gene (SEQ ID NO:2 (Type A)), the probes having C at their ends shown in table 15 were designed. In table 15, the position of each probe is indicated by its nucleotide positions in the nucleotide sequence shown in SEQ ID NO:2. Labeling with PACIFIC BLUE, TAMRA and PODIPY FL was carried out according to a conventional method.

The reagent solution was the same with those used in Example 1 except that the following probes were used. Further, Tm analysis was carried out as in Example 1.

The sequences of the complementary strand oligonucleotides used as the subjects of detection are shown in Table 1. These complementary strand oligonucleotides are sequences with mutated nucleotides corresponding to section 4 in Table 1 added.

As for 3FL-NPM1-mtD-R6 (SEQ ID NO:58), the difference in the Tm value (ΔTm) between WT and mutant Type M, N, 3, 12, and I was 4° C. or less. However, in other mutants, the significant difference in Tm value was found. Thus, the probe was proved to be suitable for detecting the mutations.

The results are shown in Table 16.

TABLE 16

| mtA-R4 probe and each Tm value | | mtB-R5 probe and each Tm value | | mtD-R6 probe and each Tm value | |
|---|---|---|---|---|---|
| Type | Tm (° C.) | ΔTm (° C.) | Type | Tm (° C.) | ΔTm (° C.) | Type | Tm (° C.) | ΔTm (° C.) |
| WT | 45 | — | WT | 42 | — | WT | 44 | — |
| A | 64 | 19 | A | 55 | 13 | A | 61 | 17 |
| B | 53 | 8 | B | 66 | 24 | B | 62 | 18 |
| D | 57 | 12 | D | 56 | 14 | D | 67 | 23 |
| C | 51 | 6 | C | 62 | 20 | C | 60 | 16 |
| M | 46 | 1 | M | 44 | 2 | M | 43 | −1 |
| N | 41 | −4 | N | 42 | 0 | N | 48 | 4 |
| Gm | 47 | 2 | Gm | 62 | 20 | Gm | 55 | 11 |
| Km | 52 | 7 | Km | 54 | 12 | Km | 63 | 19 |
| Nm | 50 | 5 | Nm | 55 | 13 | Nm | 60 | 16 |
| Om | 58 | 13 | Om | 57 | 15 | Om | 54 | 10 |
| Qm | 60 | 15 | Qm | 52 | 10 | Qm | 57 | 13 |
| 3 | 51 | 6 | 3 | 51 | 9 | 3 | 46 | 2 |
| 4 | 50 | 5 | 4 | 60 | 18 | 4 | 59 | 15 |
| 12 | 48 | 3 | 12 | 41 | −1 | 12 | 48 | 4 |
| 13 | 53 | 8 | 13 | 52 | 10 | 13 | 50 | 6 |
| G+ | 58 | 13 | G+ | 54 | 12 | G+ | 54 | 10 |
| H+ | 50 | 5 | H+ | 59 | 17 | H+ | 59 | 15 |
| I+ | 53 | 8 | I+ | 52 | 10 | I+ | 50 | 6 |
| J+ | 59 | 14 | J+ | 60 | 18 | J+ | 55 | 11 |
| I | 42 | −3 | I | 53 | 11 | I | 47 | 3 |

TABLE 15

| SEQ ID NO: | Probe name | Sequence (5'→3') | Positions | Mer |
|---|---|---|---|---|
| 56 | 3PB-NPM1-mtA-R4 | cactgcCAGAcagagatc-(PACIFIC BLUE) | 162-145 | 18 |
| 57 | 3T-NPM1-mtB-R5 | cactgcCATGcagagatc-(TAMRA) | 162-145 | 18 |
| 58 | 3FL-NPM1-mtD-R6 | cactgcCAGGcagagatc-(BODIPY FL) | 162-145 | 18 |

The excitation wavelength and the detection wavelength in the Tm analysis were 365 to 415 nm and 445 to 480 nm (PACIFIC BLUE), 520 to 555 nm and 585 to 700 nm (TAMRA), 420 to 485 nm and 520 to 555 nm (TAMRA), respectively.

By using the above-mentioned probes, as in Example 1, detection peaks (Tm values) were confirmed by Tm analysis. Further, the difference between the Tm value to the nucleotide sequence of wild type and the Tm value to the nucleotide sequence of respective mutants were confirmed.

As for 3PB-NPM1-mtA-R4 (SEQ ID NO:56), the difference in the Tm value (ΔTm) between WT and mutant Type M, N, Gm, 12, and I was 4° C. or less. However, in other mutants, the significant difference in the Tm value was confirmed. Thus, the probe was proved to be suitable for detecting the mutations.

As for 3T-NPM1-mtB-R5 (SEQ ID NO:57), the difference in the Tm value (ΔTm) between WT and mutant Type M, N, and 12 was 4° C. or less. However, in other mutants, the significant difference in Tm value was confirmed. Thus, the probe was proved to be suitable for detecting the mutations.

mtA-R4 probe is a probe with a sequence complementary to a nucleotide sequence wherein four nucleotide sequence "tctg", which is specific to Type A, was inserted into WT sequence (14 mer). Since mtA-R4 probe is identical to Type A, Type B, and Type D sequences in 18 mer, 16 mer, and 17 mer, respectively, a higher Tm value (higher affinity) is obtained compared with WT complementary strand (14 mer indentical). Thus, these mutans can be detected.

Similarly, since mtB-R5 probe, which is complementary to Type B sequence, is identical to Type A, Type B, and Type D sequences in 16 mer, 18 mer, and 17 mer, respectively, a higher Tm value is obtained compared with WT complementary strand.

Similarly, since mtD-R6 probe, which is complementary to Type D sequence, is identical to Type A, Type B, and Type D sequences in 17 mer, 17 mer, and 18 mer, respectively, a higher Tm value is obtained compared with WT complementary strand.

Example 4

Detection from Complementary Strand Oligonucleotide to Confirm Detection Sensitivity In order to study with how much proportion a mutation in exon 12 of the NPM1 gene should be contained in a sample to allow detection of the mutation, detection waveforms obtained with various mixing ratios between artificial nucleic acid plasmids with the wild-type sequence and a mutant sequence (Type A) were observed. As the artificial nucleic acids, plasmids were prepared by insertion of the wild-type sequence around exon 12 of the NPM1 gene (590 bp, SEQ ID NO:1) or the mutant type A (594 bp, SEQ ID NO:2) to pUC plasmid vector.

TABLE 17

(Reaction solution volume: 50 μl)

| | |
|---|---|
| 1x PCR buffer | |
| dNTP | 0.2 mM |
| MgCl$_2$ | 1.5 mM |
| Taq polymerase (manufactured by ARKRAY, Inc.) | 1.88 U/test |
| NPM1-F2 | 1 μM |
| NPM1-R4 | 0.5 μM |
| probe | 0.8 μM |
| Template plasmid | 4 μl |

The wild type and a mutant Type A were mixed with mixing ratios 10%, 3%, or 0% (WT100%) to prepare an artificial nucleic acid plasmid at a concentration of 500 copies/μl, and 4 μl of the resulting artificial nucleic acid plasmid was used as a template plasmid.

The PCR and Tm analysis were carried out as described in Table 11 of Example 2. The excitation wavelength and the detection wavelength in the Tm analysis were 365 to 415 nm and 445 to 480 nm (PACIFIC BLUE), 520 to 555 nm and 585 to 700 nm (TAMRA), or 420 to 485 nm and 520 to 555 nm (BODIPY FL), respectively.

Figure 39:
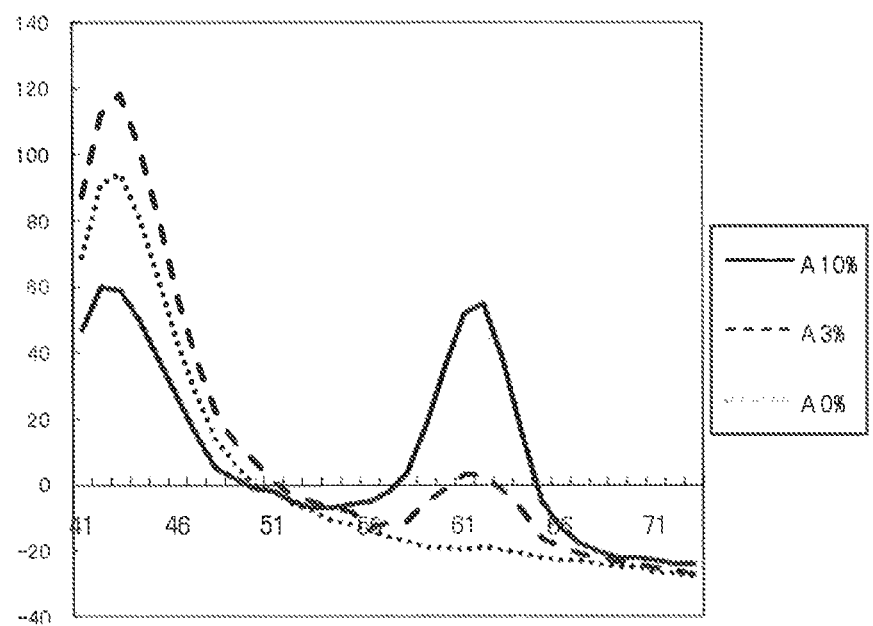
FIG. 39 shows the result of Tm analysis after PCR reaction for mt type A (plasimid) in Example 4 using PACIFIC BLUE (mtA-R4) as a probe.
Figure 40:
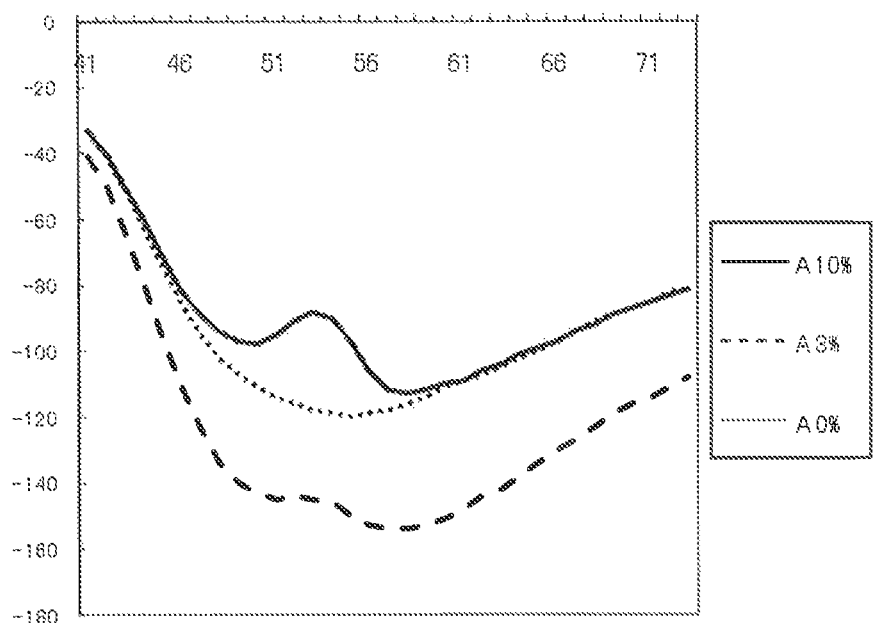
FIG. 40 shows the result of Tm analysis after PCR reaction for mt type A (plasmid) in Example 4 using TAMRA(mtB-R5) as a probe.
Figure 41:
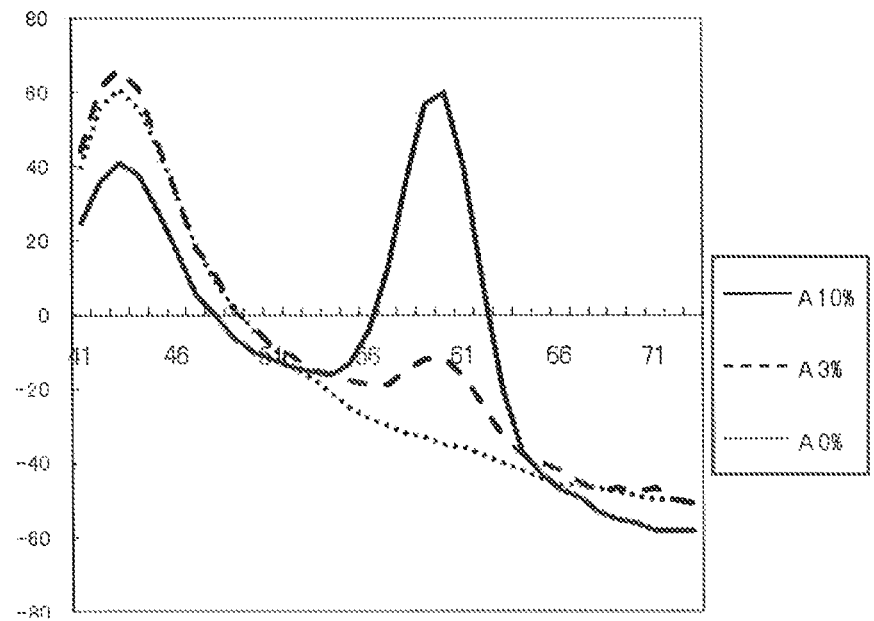
FIG. 41 shows the result of Tm analysis after PCR reaction for mt type A (plasmid) in Example 4 using BODIPY FL(mtD-R6) as a probe.

The detection peaks of mutant type A were confirmed using probes described in Table 15. In particular, a detection peak was found with mtA-R4 probe at a ratio of 10% or 3% of mutant type A at 61 to 62° C. (FIG. 39), a detection peak was found with mtB-R5 probe at a ratio of 10% of mutant type A at 53° C. (FIG. 40), and a detection peak was found with mtD-R6 probe at a ratio of 10% or 3% of mutant type A at 59 to 60° C. (FIG. 41).

Based on the results of Example 4, when mtA-R4 (SEQ ID NO:56), mtB-R5 (SEQ ID NO:57) and mtD-R6 (SEQ ID NO:58) were used, changes in the fluorescence intensity which can be analyzed by Tm analysis were observed for the polymorphisms of mutations (Type A) in exon 12 of the NPM1 gene. That is, the mutant type A has another peak in addition to the peak for the wild type, and a unique pattern of the amount of change in the fluorescence intensity exists. Therefore, by using the probes mtA-R4 (SEQ ID NO:56), mtB-R5 (SEQ ID NO:57) and mtD-R6 (SEQ ID NO:58), the polymorphisms (Type A) of mutations in exon 12 of the NPM1 gene can be detected with a high sensitivity from a small amount of sample.

By using the probe described herein, the risk of developing acute myeloid leukemia, and/or the diseased state and/or prognosis of acute myeloid leukemia may be diagnosed.

---

The invention claimed is:

1. A probe comprising a label and an oligonucleotide sequence, wherein:
the oligonucleotide sequence of the probe consists of an oligonucleotide selected from the group consisting of SEQ ID NO: 56, 57 and 58; and
the the nucleotide base at the first, second or third position from the 5' or 3' end of the oligonucleotide is labeled with a fluorescent dye.

2. The probe according to claim 1, wherein the nucleotide base at the 3' end of the oligonucleotide sequence is labeled with a fluorescent dye.

3. The probe according to claim 1, wherein the nucleotide base at the first, second or third position from the 3' end of the oligonucleotide sequence is labeled with a fluorescent dye.

4. The probe according to claim 1, wherein said probe emits fluorescence when said probe is not hybridized with a target sequence and the fluorescence intensity decreases when said probe is hybridized with said target sequence.

5. The probe according to claim 1, wherein said probe is a probe for melting curve analysis.

6. A method of analyzing a polymorphism in exon 12 of the NPM1 gene, comprising:
(I) adding the probe according to claim 1 to a sample comprising nucleic acid, to allow said probe to hybridize with said nucleic acid;
(II) changing the temperature to dissociate the hybrid-forming body between said nucleic acid and said probe, and measuring fluctuation of a signal due to the dissociation of said hybrid-forming body;
(III) analyzing said fluctuation of a signal to detect the Tm value of single-stranded nucleic acid in said sample; and
(IV) determining based on said Tm value the presence or absence of said polymorphism or the abundance ratio of single-stranded nucleic acid having said polymorphism in single-stranded nucleic acid in said sample.

7. The method according to claim 6, further comprising amplifying DNA before Step (I) or at the same time with Step (I).

8. A method of analyzing the risk of developing acute myeloid leukemia, and/or the progression of acute myeloid leukemia and/or prognosis of acute myeloid leukemia comprising detecting a polymorphism in exon 12 of the NPM1 gene and determining the presence or absence of the polymorphism using the method according to claim 6.

9. A reagent kit for detecting a polymorphism in the NPM1 gene, comprising the probe according to claim 1.

10. The reagent kit according to claim 9, further comprising primers for amplifying a region comprising a sequence in the nucleotide sequence shown in SEQ ID NO: 1 in the NPM1 gene, with which the probe according to claim 1 hybridizes.

11. The reagent kit according to claim 10, wherein said primers comprise SEQ ID NO: 16 and 17.

12. The probe according to claim 1, wherein the oligonucleotide sequence of the probe consists of SEQ ID NO: 56.

13. The probe according to claim 1, wherein the oligonucleotide sequence of the probe consists of SEQ ID NO: 56 and the oligonucleotide sequence is labeled with the fluorescent dye at the 3' end.

* * * * *